(12) United States Patent
Nagao et al.

(10) Patent No.: US 7,989,802 B2
(45) Date of Patent: Aug. 2, 2011

(54) LIGHT EMITTING DEVICE MATERIAL AND LIGHT EMITTING DEVICE

(75) Inventors: Kazumasa Nagao, Otsu (JP); Tsuyoshi Tominaga, Otsu (JP)

(73) Assignee: Toray Industries, Inc., Tokyo (JP)

( * ) Notice: Subject to any disclaimer, the term of this patent is extended or adjusted under 35 U.S.C. 154(b) by 124 days.

(21) Appl. No.: 12/529,829

(22) PCT Filed: Feb. 28, 2008

(86) PCT No.: PCT/JP2008/053464
§ 371 (c)(1), (2), (4) Date: Sep. 3, 2009

(87) PCT Pub. No.: WO2008/108256
PCT Pub. Date: Sep. 12, 2008

(65) Prior Publication Data
US 2010/0038634 A1 Feb. 18, 2010

(30) Foreign Application Priority Data
Mar. 7, 2007 (JP) .................................. 2007-056814

(51) Int. Cl.
*H01L 51/54* (2006.01)
(52) U.S. Cl. ...................... 257/40; 257/79; 257/E51.041
(58) Field of Classification Search .................... 257/40, 257/79, E51.041
See application file for complete search history.

(56) References Cited

FOREIGN PATENT DOCUMENTS

| JP | 2000-273056 | 10/2000 |
|---|---|---|
| JP | 2002-063988 | 2/2002 |
| JP | 2004-075567 | 3/2004 |
| JP | 2004-139957 | 5/2004 |
| JP | 2007-077094 A | 3/2007 |
| JP | 2007-169581 A | 7/2007 |
| JP | 2007-238500 A | 9/2007 |
| JP | 2008-078362 A | 4/2008 |
| WO | WO 2004-096945 A1 | 11/2004 |
| WO | WO 2006-128800 A1 | 12/2006 |
| WO | WO 2007-029798 A1 | 3/2007 |

OTHER PUBLICATIONS

International Search Report dated May 20, 2008, application No. PCT/JP2008/053464.
"Organic Electroluminescent Diodes", Applied Physics Letters (U.S.), C.W. Tang and S.A. VanSlyke, 1987, vol. 51, No. 12, pp. 913-915.

*Primary Examiner* — Long Pham
(74) *Attorney, Agent, or Firm* — RatnerPrestia

(57) ABSTRACT

A light emitting device material comprises a pyrene compound represented by formula (1) below. Also disclosed is a light emitting device using such a material. ($R^1$ to $R^{17}$ may be the same or different and are each selected from the group consisting of hydrogen, an alkyl group, a cycloalkyl group, a heterocyclic group, an alkoxy group, an alkylthio group, an aryl ether group, an aryl thioether group, an aryl group, a heteroaryl group, an amino group, a silyl group, —P(=O)$R^{18}R^{19}$, and a ring structure formed together with an adjacent substituent; $R^{18}$ and $R^{19}$ are each selected from an aryl group and a heteroaryl group; n is an integer of 1 to 2; and X is selected from the group consisting of a single bond, an arylene group and a heteroarylene group, provided that at least one of $R^{10}$ to $R^{17}$ is used to link to X.)

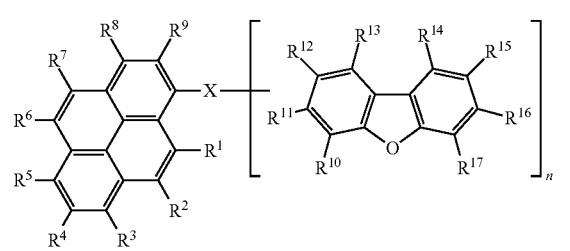

(1)

9 Claims, No Drawings

LIGHT EMITTING DEVICE MATERIAL AND LIGHT EMITTING DEVICE

This application is a U.S. National Phase Application of PCT International Application No. PCT/JP2008/053464, filed Feb. 28, 2008, which claims priority to Japanese Patent Application No. 2007-056814, filed Mar. 7, 2007, the contents of all applications being incorporated by reference herein in their entirety.

FIELD OF THE INVENTION

The invention relates to a pyrene compound useful as a fluorescent dye or a charge transporting material and to a light emitting device that uses the pyrene compound and is useful in the field of display devices, flat panel displays, backlights, illuminations, interiors, signs, billboards, electro-photographic machines, optical signal generators, and so on.

BACKGROUND OF THE INVENTION

In recent years, organic thin-film light emitting devices have been actively studied, which emit light when electrons injected from a cathode and holes injected from an anode are recombined in an organic luminous body placed between the electrodes. Such light emitting devices are attracting attention, because they are thin and characterized by high-luminance light emission at low driving voltage and multicolor light emission from selected emissive materials.

Since C. W. Tang et al. of the Eastman Kodak Company reported an organic thin-film light emitting device capable of emitting light with high luminance, many research institutes have conducted the research. The typical structure of the organic thin-film light emitting device proposed by the research group of the Eastman Kodak Company includes an ITO glass substrate, and a hole transporting diamine compound, an emissive layer of tris(8-quinolinolato)aluminum (III), and a cathode of Mg:Ag (alloy) sequentially provided on the substrate, which was capable of emitting 1,000 cd/m$^2$ of green light at a driving voltage of about 10 V (see Applied Physics Letters (U.S.), 1987, Vol. 51, No. 12, pp. 913-915.).

Organic thin-film light emitting devices have also been actively studied for display applications and so on, because they can emit light of different colors, when different fluorescent materials are used in the emissive layer. Among emissive materials of three primary colors, the research of green emissive materials is most advanced. Now, active researches have been conducted to improve the properties of red and blue emissive materials.

One of the most important objects in organic thin-film light emitting devices is to allow the devices to have satisfactory luminance efficiency and durability at the same time. Particularly for blue light emitting devices, few blue emissive materials can form a device with a high level of durability and reliability. For example, there are disclosed blue light emitting devices using aryl-substituted pyrene compounds (see Japanese Patent Application Laid-Open (JP-A) No. 2000-273056 (claims 1 and 2), JP-A No. 2002-63988 (claim 1), JP-A No. 2004-75567 (claims 1 to 4) and JP-A No. 2004-139957 (claim 1)). There is also disclosed a blue light emitting device using a pyrene compound having four dibenzofuranyl groups (see PCT pamphlet of International Publication No. 2004/096945 (claims)). However, these devices all have insufficient durability.

SUMMARY OF THE INVENTION

As mentioned above, blue light emitting devices having high luminance efficiency and good durability are not available from conventional organic thin-film light emitting devices. The invention provides a light emitting device material that makes it possible to produce a blue light emitting device having high luminance efficiency and good durability, and provides a light emitting device using such a material.

An embodiment of the invention provides a light emitting device material including a pyrene compound represented by formula (I):

[Formula 1]

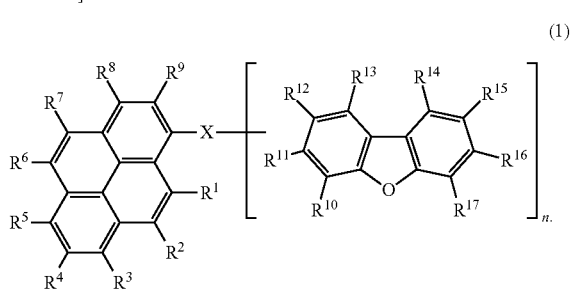

(1)

$R^1$ to $R^{17}$ may be the same or different and are each selected from the group consisting of hydrogen, an alkyl group, a cycloalkyl group, a heterocyclic group, an alkoxy group, an alkylthio group, an aryl ether group, an aryl thioether group, an aryl group, a heteroaryl group, an amino group, a silyl group, —P(=O)$R^{18}R^{19}$, and a ring structure formed together with an adjacent substituent; $R^{18}$ and $R^{19}$ are each selected from an aryl group and a heteroaryl group; n is an integer of 1 to 2; and X is selected from the group consisting of a single bond, an arylene group and a heteroarylene group, provided that at least one of $R^{10}$ to $R^{17}$ is used to link to X.

Another embodiment of the invention provides a light emitting device including an anode, a cathode and at least an emissive layer interposed between the anode and the cathode, the emissive layer emitting light by electric energy, wherein the light emitting device includes the light emitting device material represented by formula (I).

According to an embodiment of the invention, there is provided a light emitting device material that is useful for light emitting devices and so on and has high thin-film stability. There is also provided a light emitting device having high luminance efficiency and good durability.

DETAILED DESCRIPTION OF THE INVENTION

A description is given of the pyrene compound represented by formula (1) for use in an embodiment of the invention.

[Formula 2]

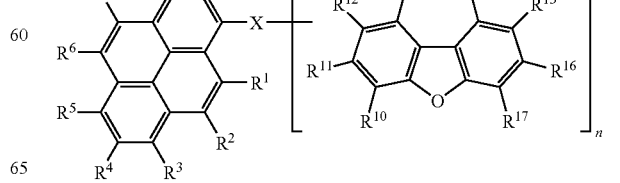

(1)

In an embodiment of the invention, the pyrene compound represented by formula (1) has a pyrene skeleton and one or two electron-donating condensed aromatic dibenzofuran skeletons in the molecule, so that it can have heat resistance and charge transporting performance at the same time. The linking group X is a single bond, an arylene group or a heteroarylene group. The linking group X is preferably an arylene group or a heteroarylene group. When X is an arylene or heteroarylene group, a stable thin film can be formed to allow long-life light emission. In particular, X is more preferably an arylene group, because of easy availability of the raw material and easiness of the synthesis. As used herein, the term "arylene group" refers to a divalent or trivalent group derived from an aromatic hydrocarbon group, such as a phenylene, naphthylene, biphenylene, phenanthrylene, terphenylene, or pyrenylene group, which may be substituted or unsubstituted. The number of the carbon atoms in the arylene group is generally, but not limited to, in the range of 6 to 40. The arylene group is more preferably a divalent group derived from a phenyl group (a phenylene group).

The term "heteroarylene group" refers to a divalent or trivalent group derived from an aromatic group having an atom or atoms other than carbon in addition to a carbon atom or atoms, such as a furanylene, thiophenylene, oxazolylene, pyridylene, quinolinylene, or carbazolylene group. The heteroarylene group may be substituted or unsubstituted. The number of the carbon atoms in the heteroarylene group is generally, but not limited to, in the range of 2 to 30.

In formula (1), $R^1$ to $R^{17}$ may be the same or different and are each selected from the group consisting of hydrogen, an alkyl group, a cycloalkyl group, a heterocyclic group, an alkoxy group, an alkylthio group, an aryl ether group, an aryl thioether group, an aryl group, a heteroaryl group, an amino group, a silyl group, —P(=O)$R^{18}R^{19}$, and a ring structure formed together with an adjacent substituent; $R^{18}$ and $R^{19}$ are each selected from an aryl group and a heteroaryl group; n is an integer of 1 to 2; and X is selected from the group consisting of a single bond, an arylene group and a heteroarylene group, provided that at least one of $R^{10}$ to $R^{17}$ is used to link to X.

Concerning the substituents, the term "alkyl group" refers to a saturated aliphatic hydrocarbon group such as a methyl, ethyl, n-propyl, isopropyl, n-butyl, sec-butyl, isobutyl, tert-butyl, n-pentyl, n-hexyl, n-heptyl, or n-octyl group, which may be substituted or unsubstituted. When substituted, an additional substituent is not specifically limited and includes, for example, an alkyl, aryl or heteroaryl group, and this also applies to the cases described below. The number of the carbon atoms in the alkyl group is generally, but not limited to, in the range of 1 to 20, preferably in the range of 1 to 8. The alkyl group is more preferably a methyl, ethyl, isopropyl, sec-butyl, or tert-butyl group.

The term "cycloalkyl group" refers to a saturated alicyclic hydrocarbon group such as a cyclopropyl, cyclohexyl, norbornyl, or adamanthyl group, which may be substituted or unsubstituted. The number of the carbon atoms in the alkyl moiety is generally, but not limited to, in the range of 3 to 20.

The term "heterocyclic group" refers to an aliphatic ring having an atom or atoms other than carbon in the ring, such as a pyran ring, a piperidine ring, or a cyclic amide. The heterocyclic group may be substituted or unsubstituted. The number of the carbon atoms in the heterocyclic group is generally, but not limited to, in the range of 2 to 20.

The term "alkoxy group" refers to a functional group having an aliphatic hydrocarbon group linked through an ether bond, such as a methoxy, ethoxy, or propoxy group, in which the aliphatic hydrocarbon group may be substituted or unsubstituted. The number of the carbon atoms in the alkoxy group is generally, but not limited to, in the range of 1 to 20.

The term "alkylthio group" refers to an alkoxy group analogue in which a sulfur atom replaces the oxygen atom of the ether bond. The hydrocarbon group of the alkylthio group may be substituted or unsubstituted. The number of the carbon atoms in the alkylthio group is generally, but not limited to, in the range of 1 to 20.

The term "aryl ether group" refers to a functional group having an aromatic hydrocarbon group linked through an ether bond, such as a phenoxy group, in which the aromatic hydrocarbon group may be substituted or unsubstituted. The number of the carbon atoms in the aryl ether group is generally, but not limited to, in the range of 6 to 40.

The term "aryl thioether group" is an aryl ether group analogue in which a sulfur atom replaces the oxygen atom of the ether bond. The aromatic hydrocarbon group of the aryl ether group may be substituted or unsubstituted. The number of the carbon atoms in the aryl ether group is generally, but not limited to, in the range of 6 to 40.

The term "aryl group" refers to an aromatic hydrocarbon group such as a phenyl, naphthyl, biphenyl, anthracenyl, phenanthryl, terphenyl, or pyrenyl group. The aryl group may be substituted or unsubstituted. In view of charge transporting performance, the aryl group is more preferably unsubstituted or substituted with a methyl group. The number of the carbon atoms in the aryl group is generally, but not limited to, in the range of 6 to 40. In view of heat resistance, the aryl group is more preferably unsubstituted or an alkyl-substituted phenyl or naphthyl group.

The term "heteroaryl group" refers to a five-membered ring aromatic group having one atom other than carbon in the ring, such as a furanyl, thiophenyl, pyrrolyl, benzofuranyl, benzothiophenyl, or indolyl group, or a six-membered ring aromatic group having one or more atoms other than carbon in the ring, such as a pyridyl or quinolinyl group. The heteroaryl group may be substituted or unsubstituted. In view of charge transporting performance, the heteroaryl group is more preferably unsubstituted or substituted with a methyl group. The number of the carbon atoms in the heteroaryl group is generally, but not limited to, in the range of 2 to 30.

The amino group or —P(=O)$R^{18}R^{19}$ may be substituted or unsubstituted. Examples of the substituent include alkyl, cycloalkyl, aryl, and heteroaryl groups. These substituents may be further substituted.

$R^{18}$ and $R^{19}$ are each a group selected from an aryl group and a heteroaryl group.

The term "silyl group" refers to a functional group having a bond to a silicon atom, such as a trimethylsilyl group, which may be substituted or unsubstituted. The number of the carbon atoms in the silyl group is generally, but not limited to, in the range of 3 to 20. The number of the silicon atoms is generally from 1 to 6.

Concerning formula (I), for example, the term "ring structure formed together with an adjacent substituent" refers to a conjugated or non-conjugated condensed ring that is formed when any two adjacent substituents selected from $R^1$ to $R^{17}$ (for example, $R^1$ and $R^2$) are bonded together. The condensed ring may also contain a nitrogen, oxygen, sulfur, phosphorus, or silicon atom as a constituent element of the condensed ring in addition to carbon. A condensed ring may be further condensed with another ring.

In the pyrene compound represented by formula (1) according to an embodiment of the invention, at least one of $R^3$ and $R^5$ is preferably an aryl or heteroaryl group. In this case, the intermolecular interaction between the pyrene skeletons is reduced so that the compound in the form of a solid or a thin film can maintain strong fluorescence intensity and emit light with high efficiency. In particular, $R^5$ is more preferably an aryl or heteroaryl group, so that the synthesis process can be simplified to allow low-cost production.

In the pyrene compound represented by formula (1), $R^3$ and $R^5$ are each preferably hydrogen, and $R^4$ is preferably an alkyl group. In this case, a highly-amorphous, more stable thin film can be formed. In particular, $R^8$ is more preferably an aryl or heteroaryl group, so that the intermolecular interaction can be reduced, which makes it possible to emit light with high efficiency.

Examples of the pyrene compound describe above include, but are not limited to, the compounds shown below.

[Formula 3]

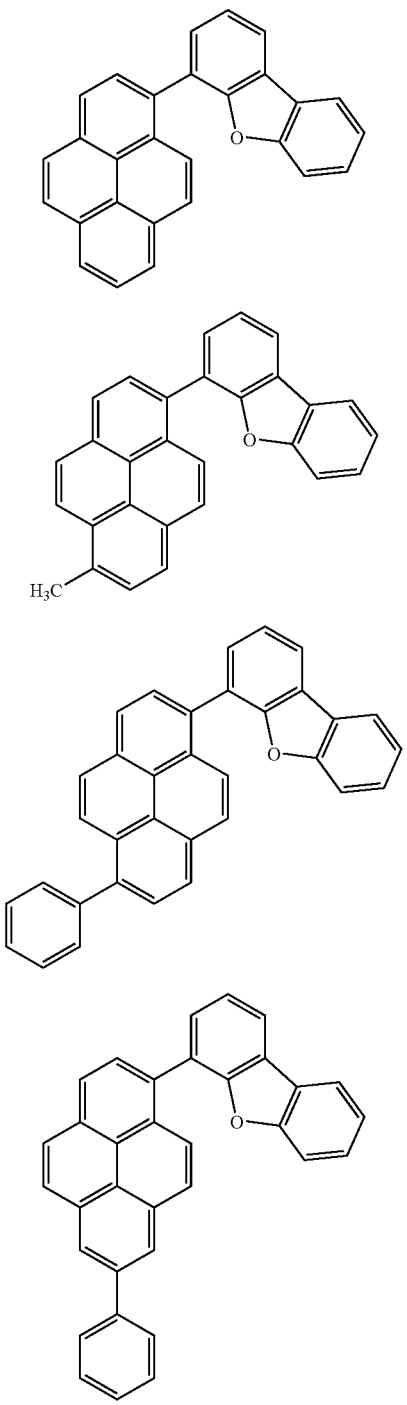
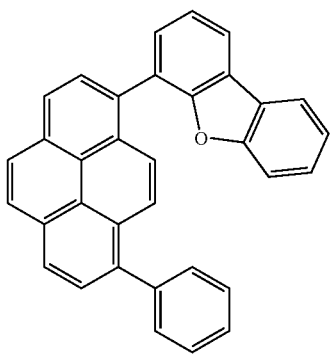
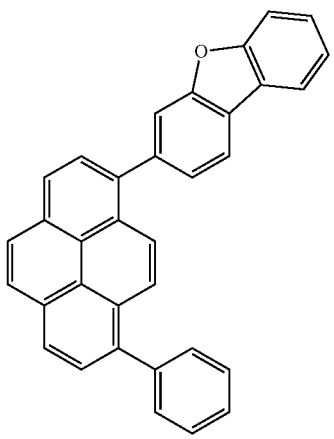
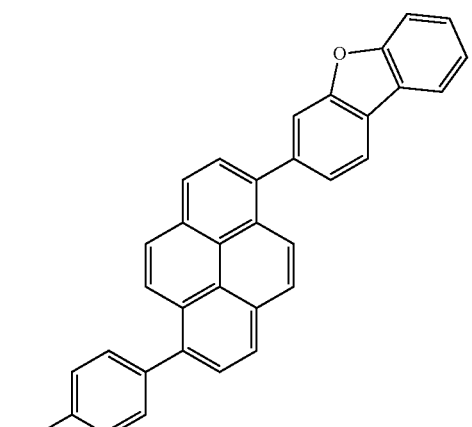
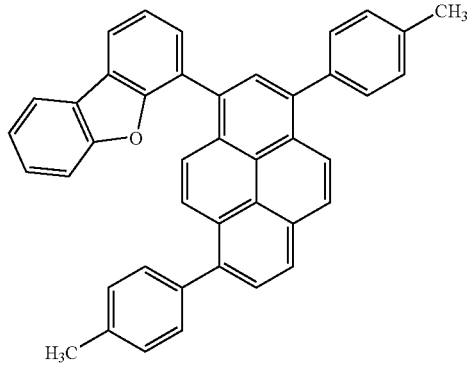

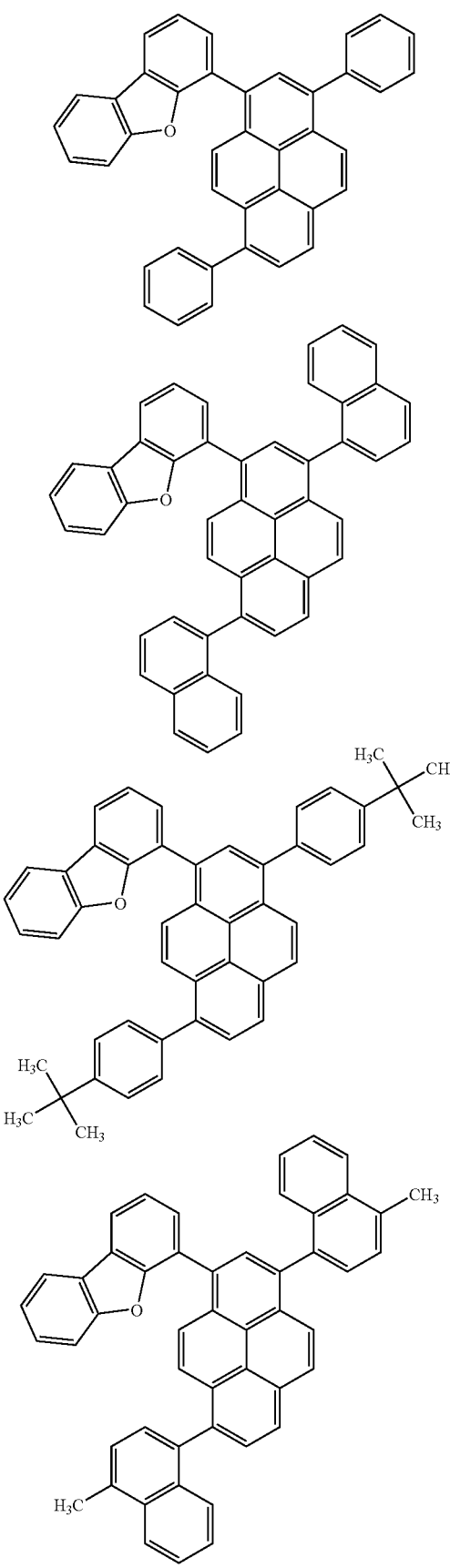
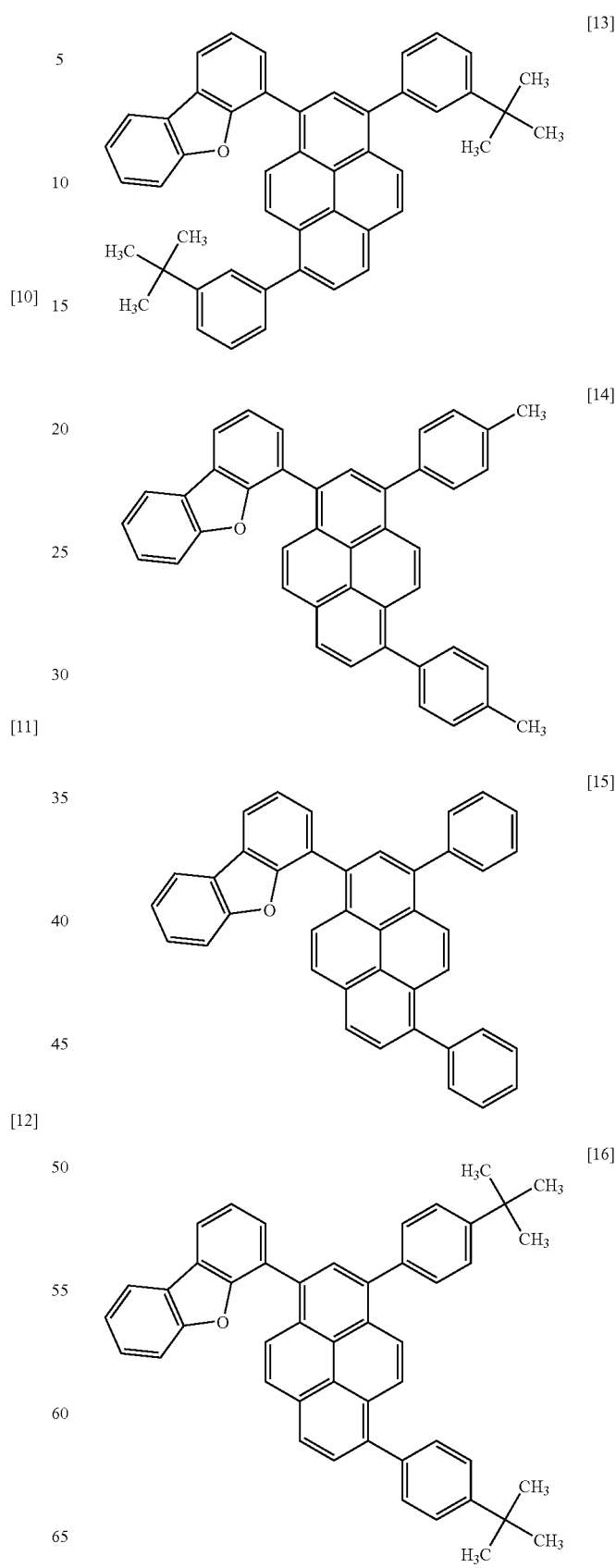

[17]
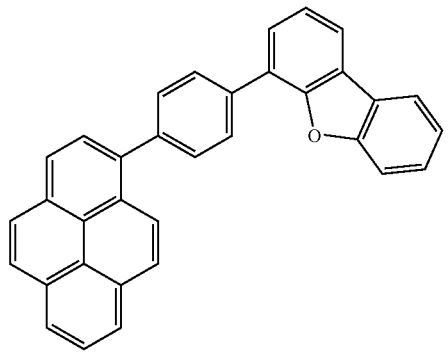
[18]
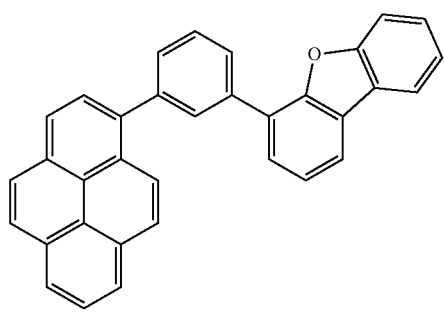
[19]
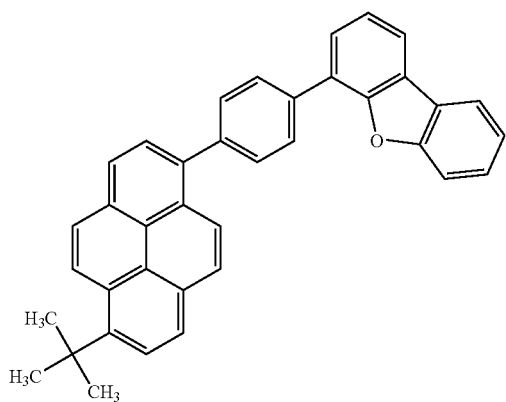
[20]
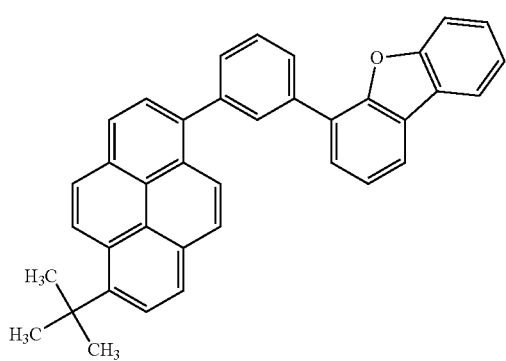
[21]
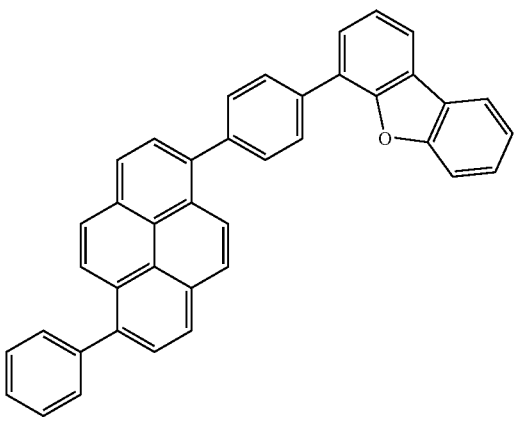
[22]
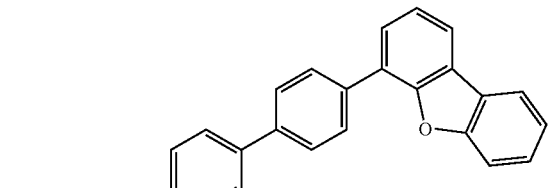
[23]
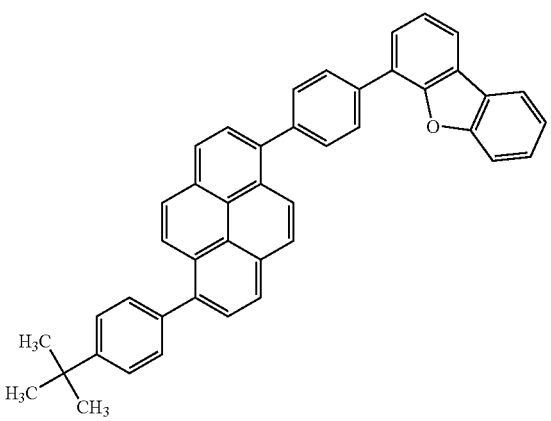

[24]
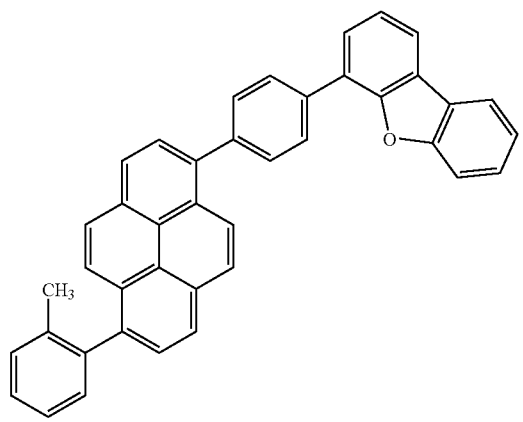
[27]
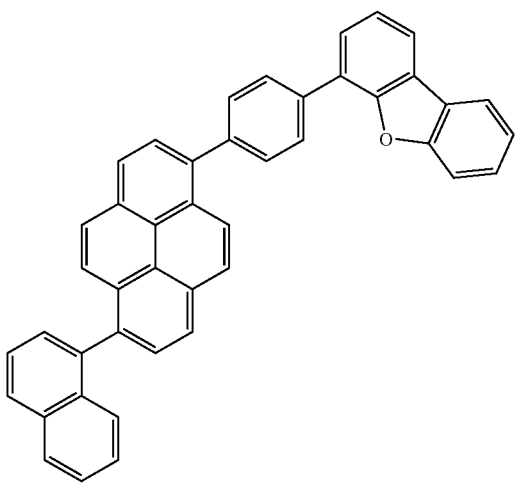
[Formula 5]
[25]
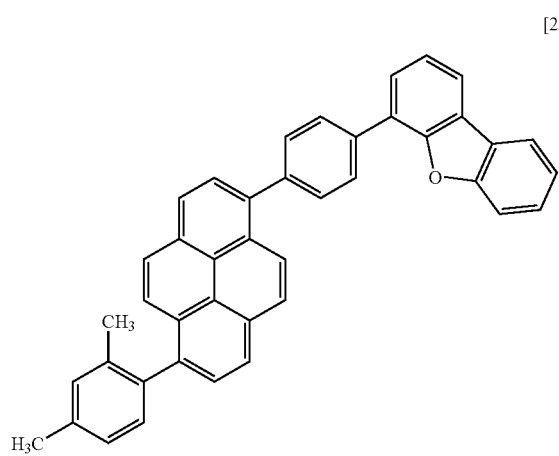
[28]
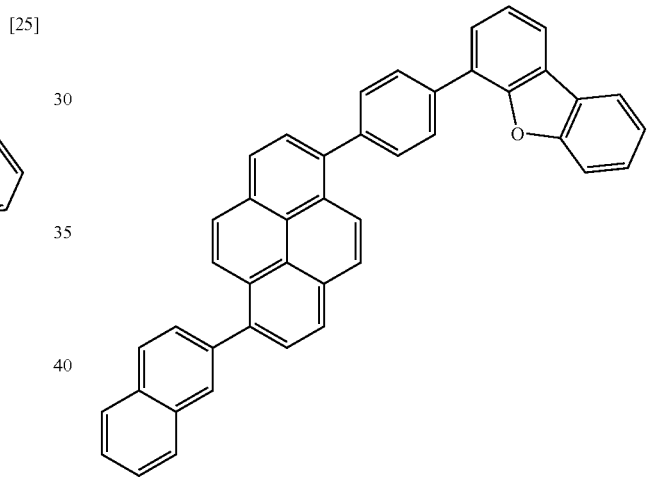
[26]
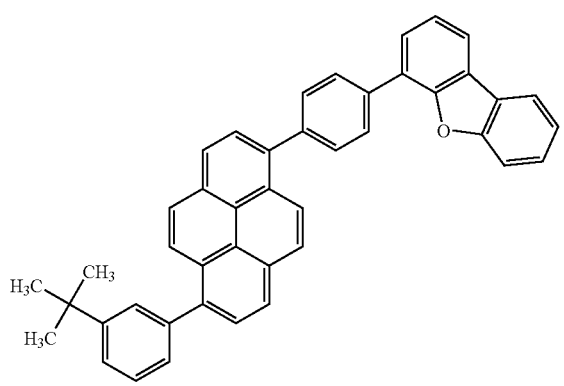
[29]
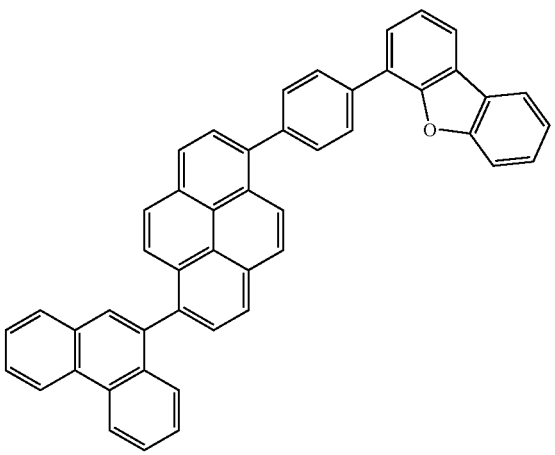

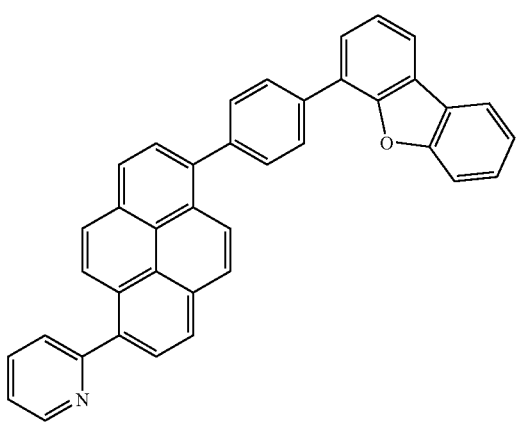
[30]
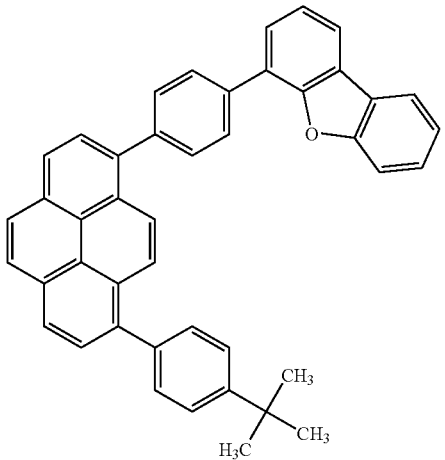
[33]
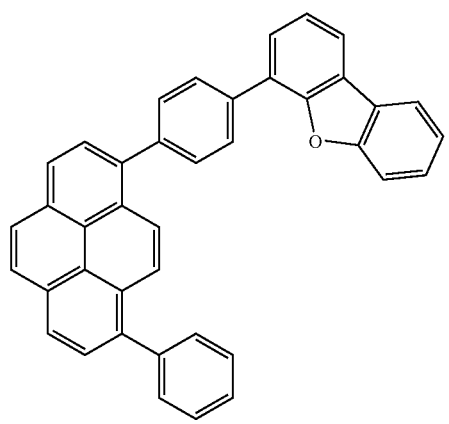
[31]
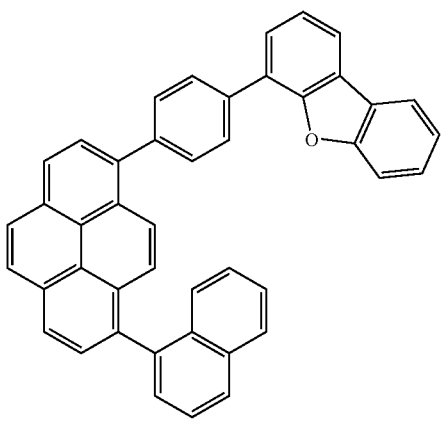
[34]
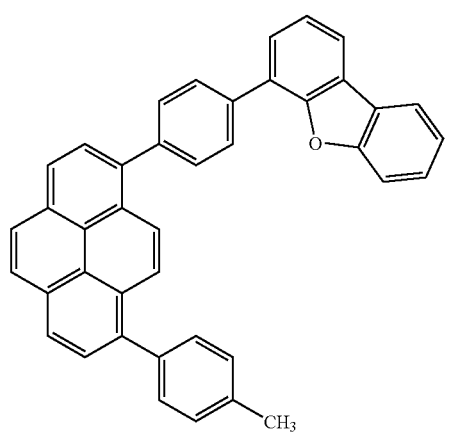
[32]
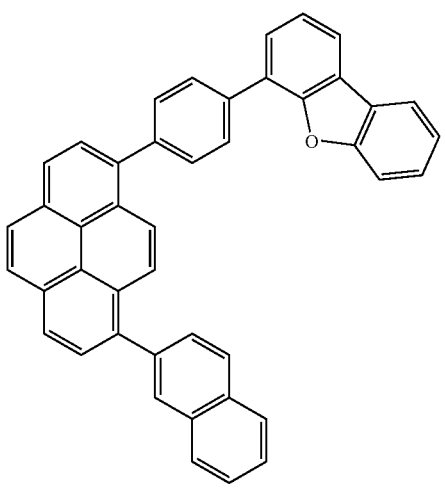
[35]

[36]
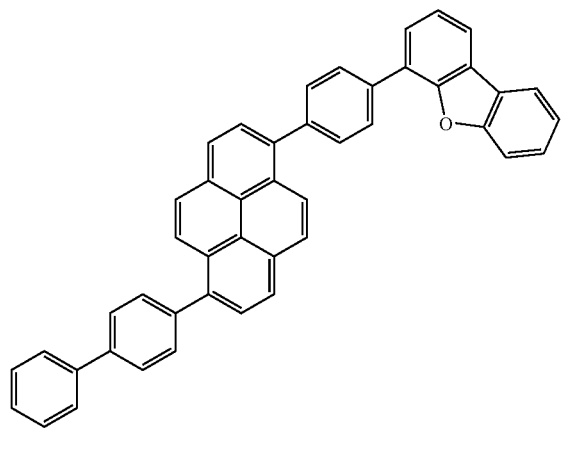
[Formula 6]
[37]
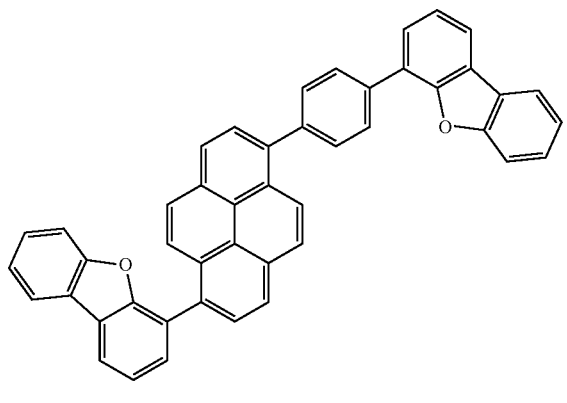
[38]
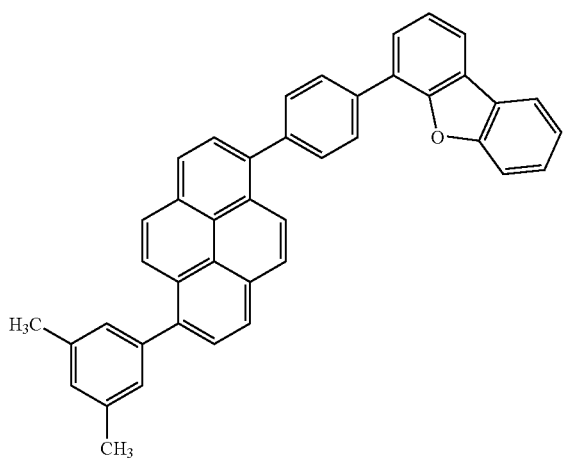
[39]
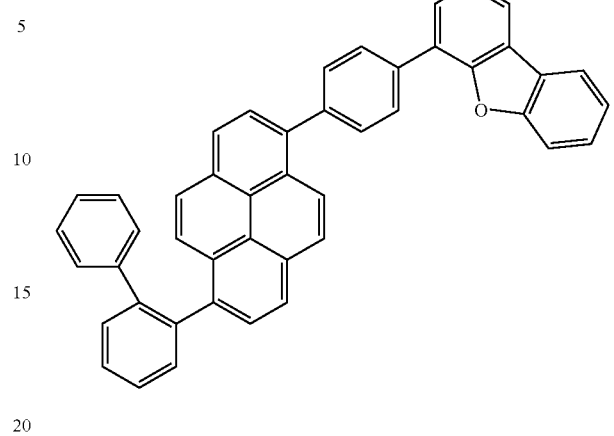
[40]
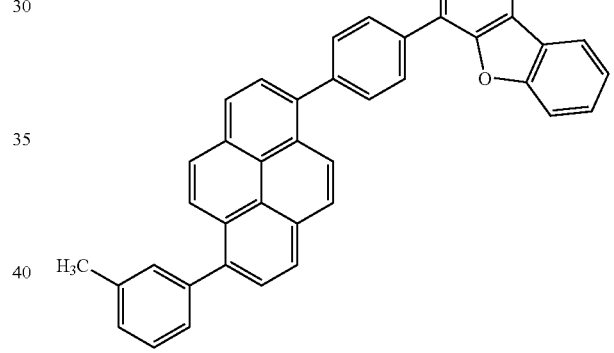
[41]
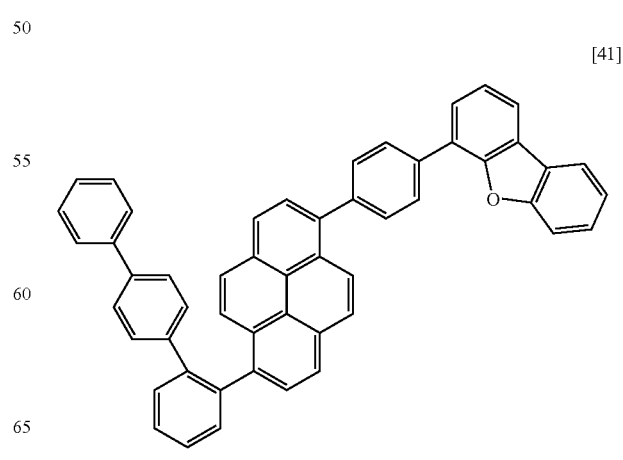

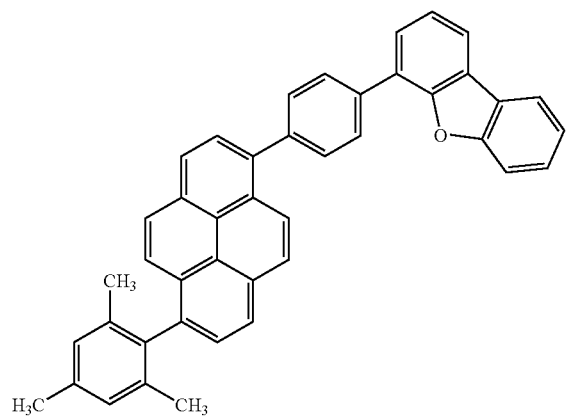
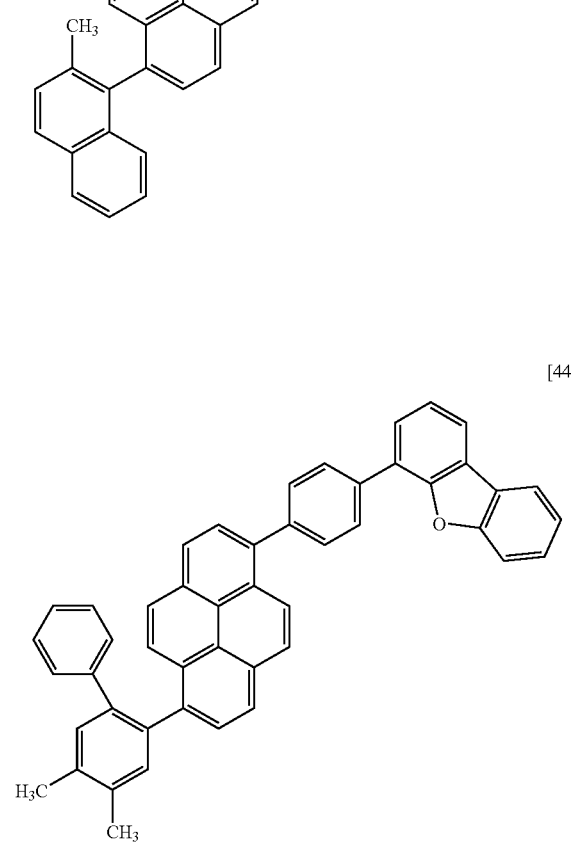
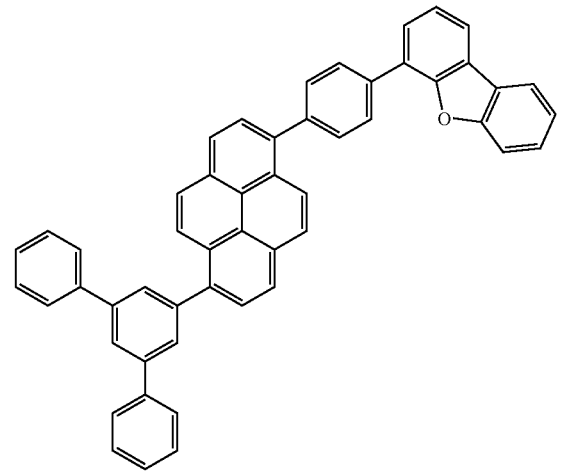

[49] 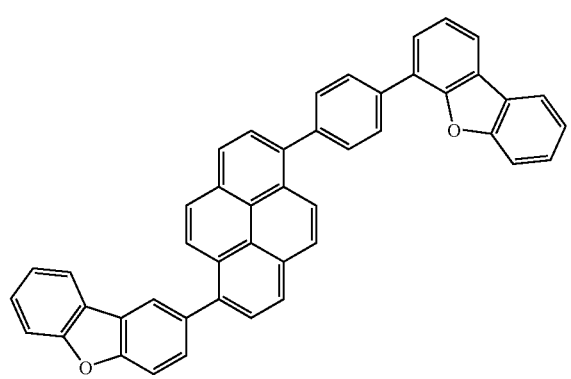
[50] 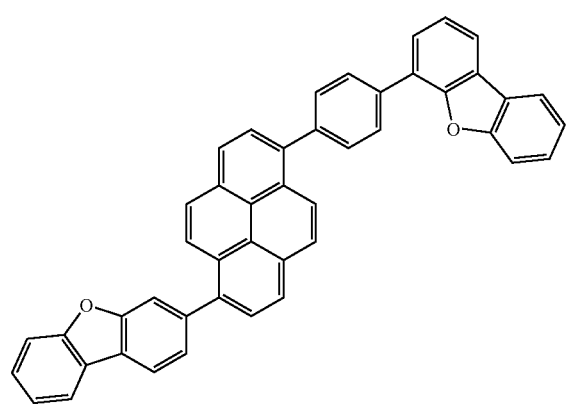
[51] 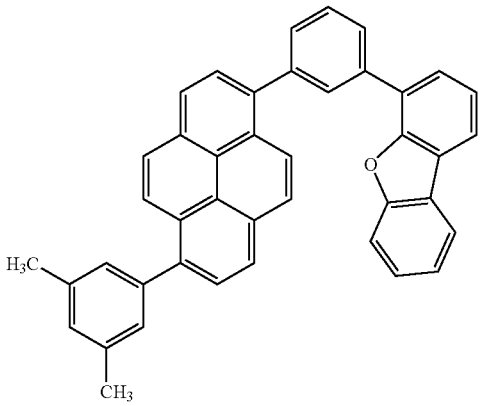
[52] 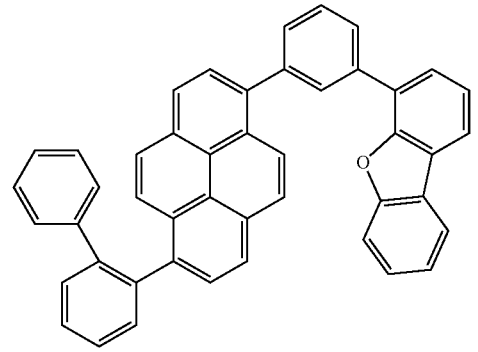
[53] 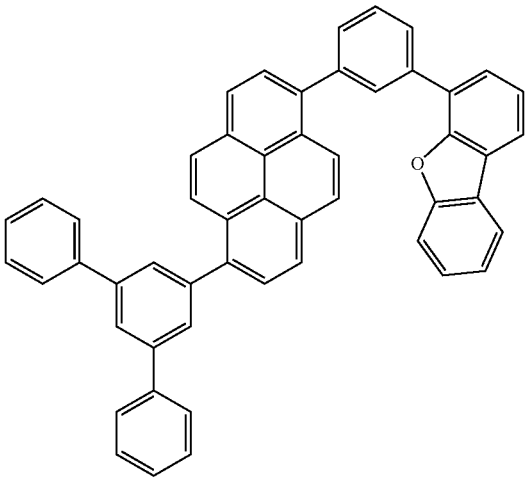
[54] 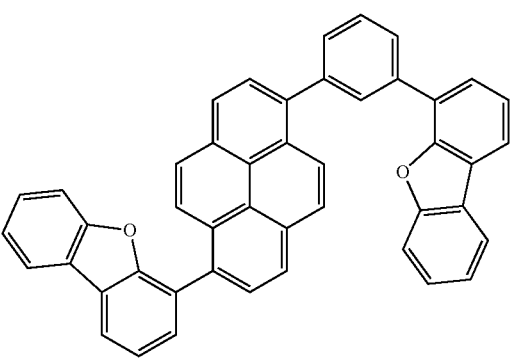
[55]
[56]

[57]
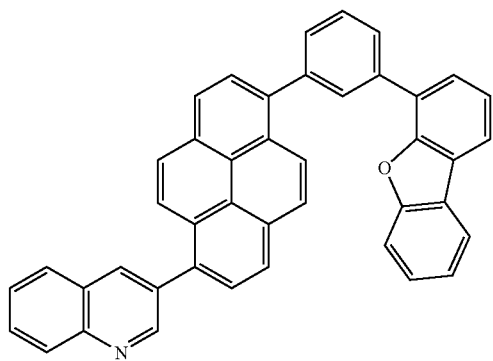
[Formula 8]
[58]
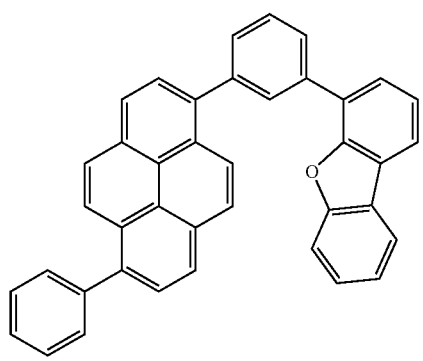
[59]
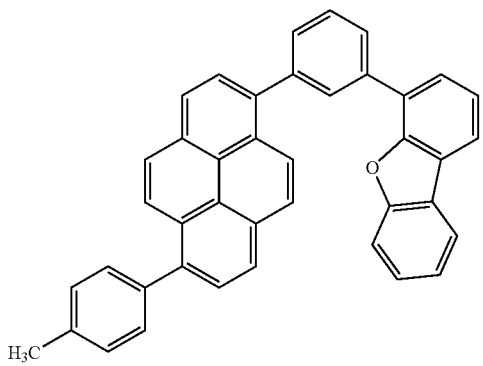
[60]
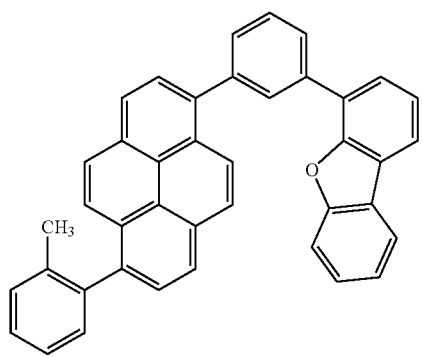
[61]
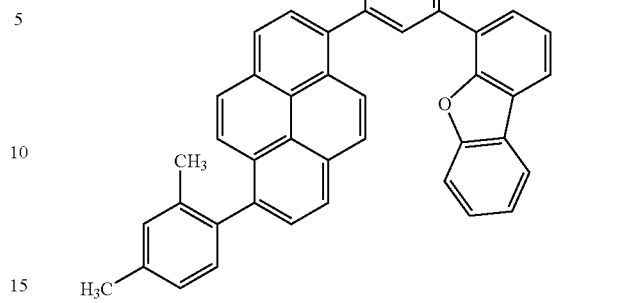
[62]
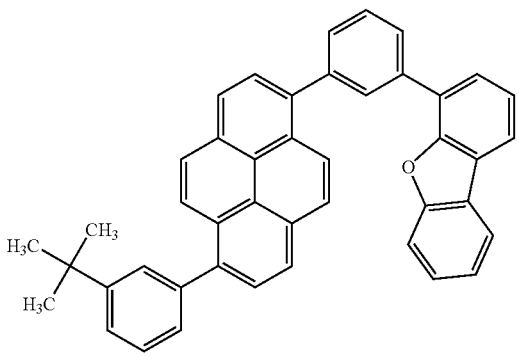
[63]
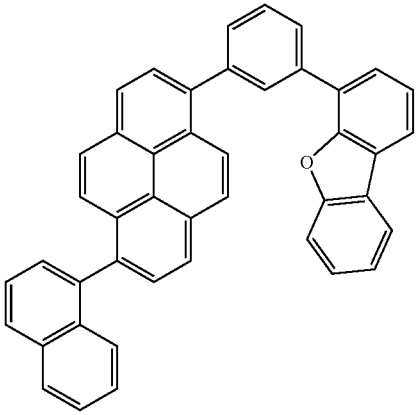
[64]
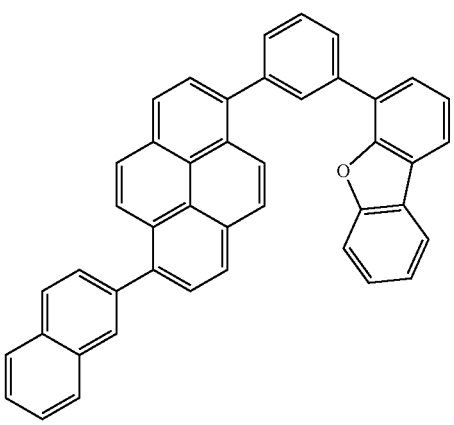

[65]
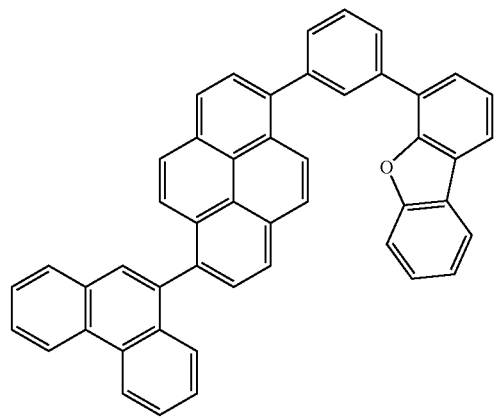
[66]
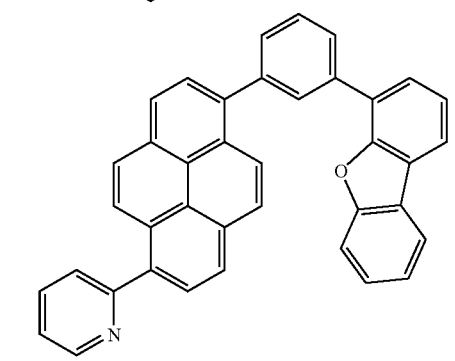
[67]
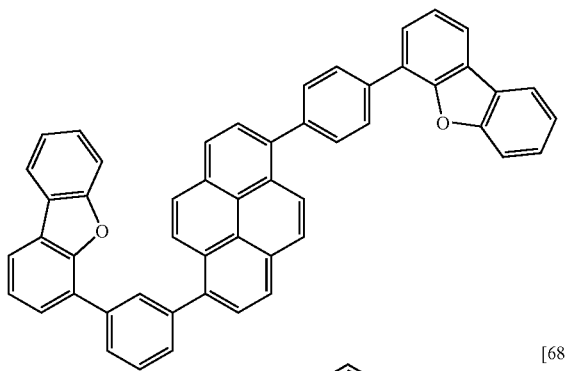
[68]
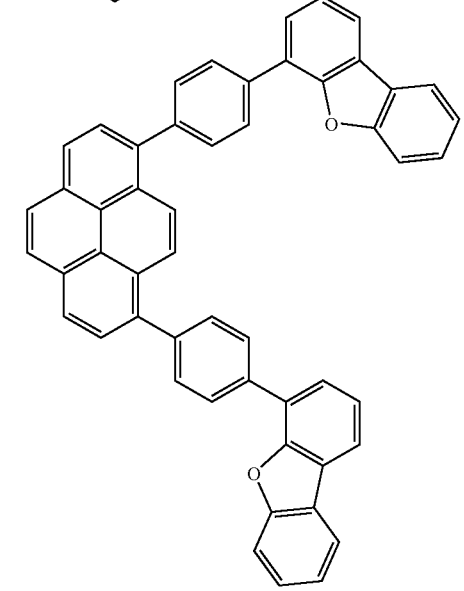
[69]
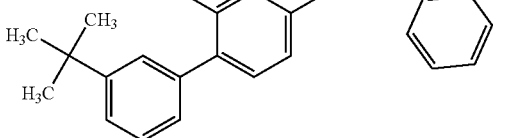
[Formula 9]
[70]
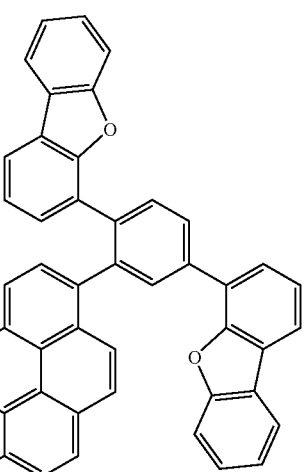
[71]
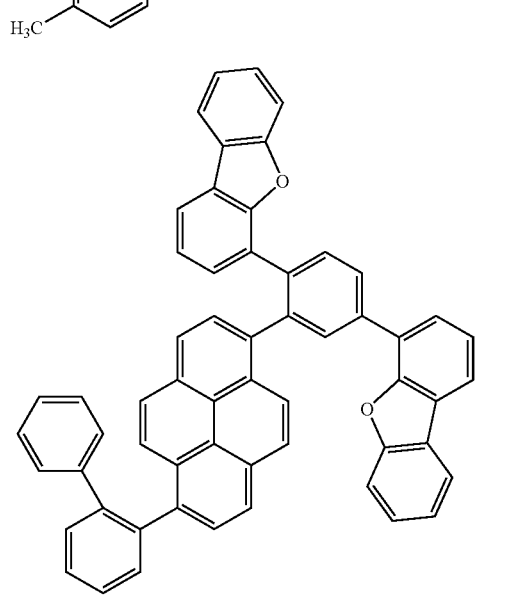

[72]
[73]
[74]
[75]
[76]
[77]
[78]
[79]
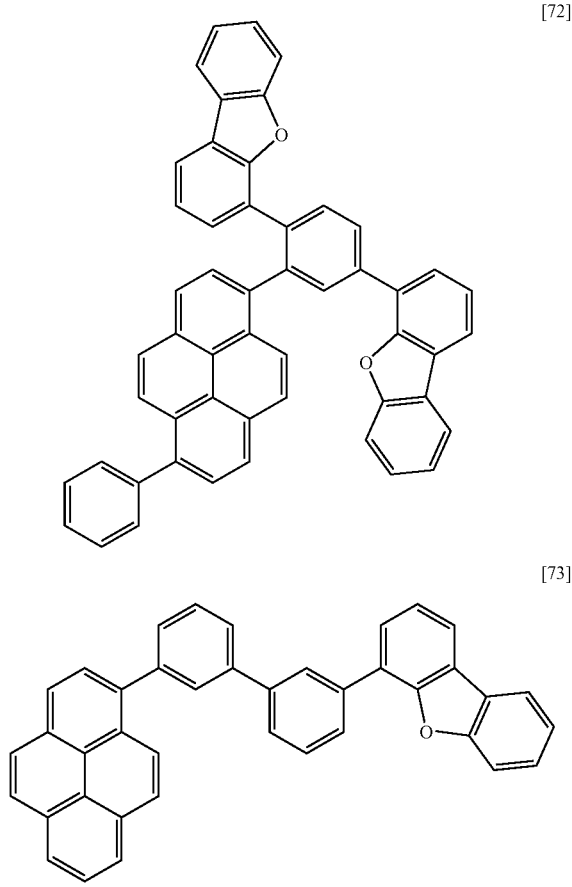
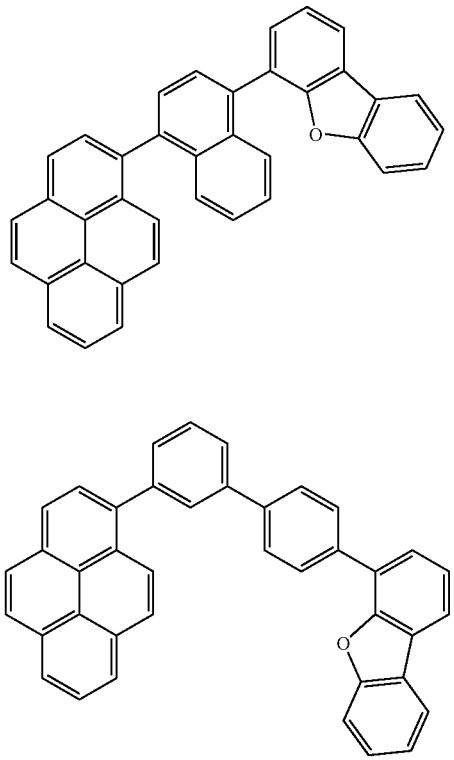

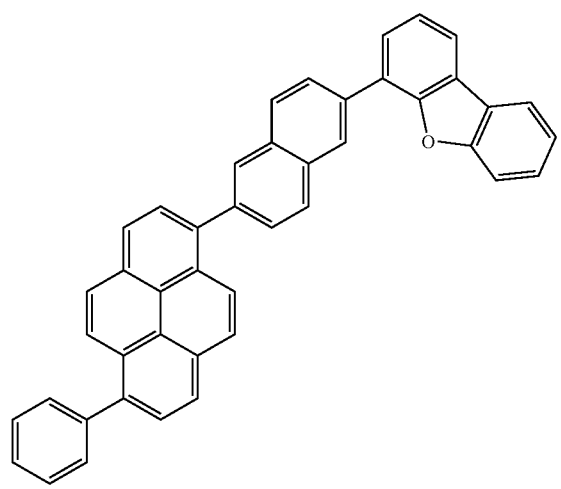
[80]
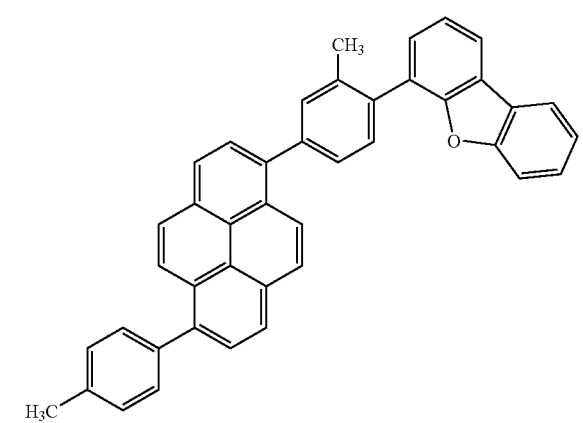
[83]
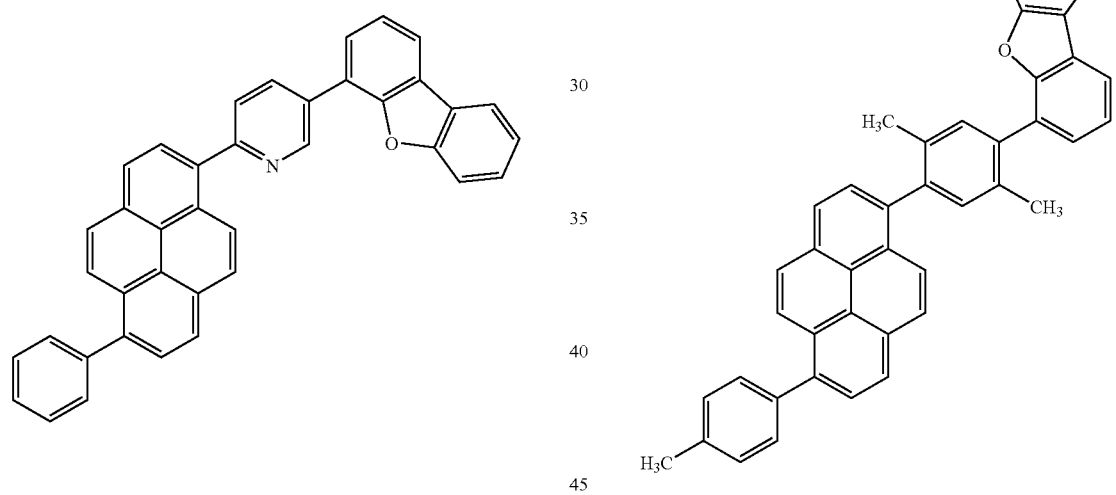
[81] [84]
[Formula 10]
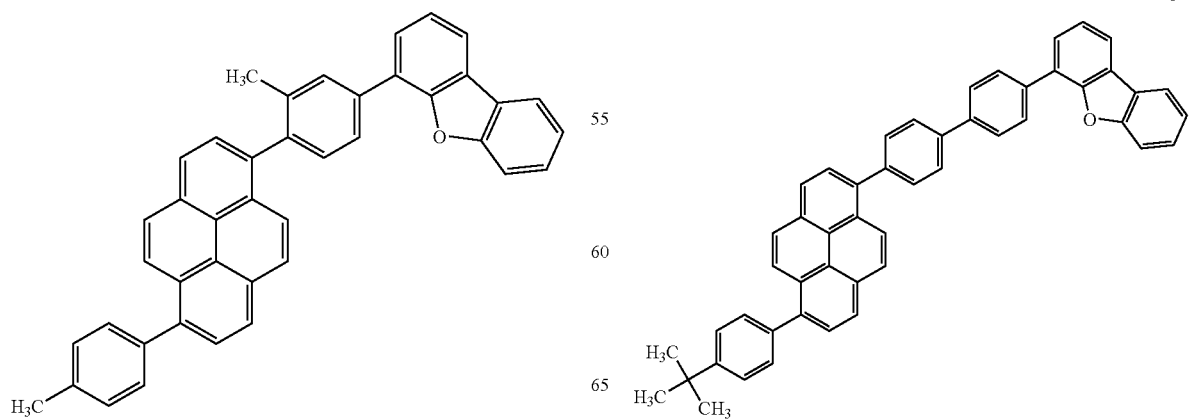
[82] [85]

[86]
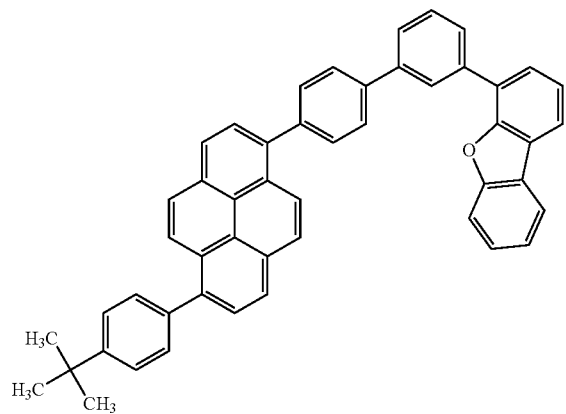
[89]
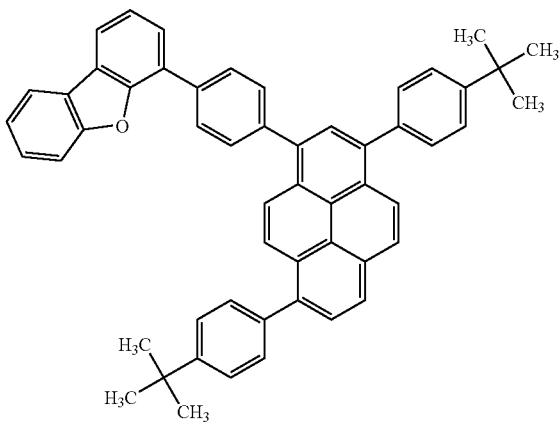
[87]
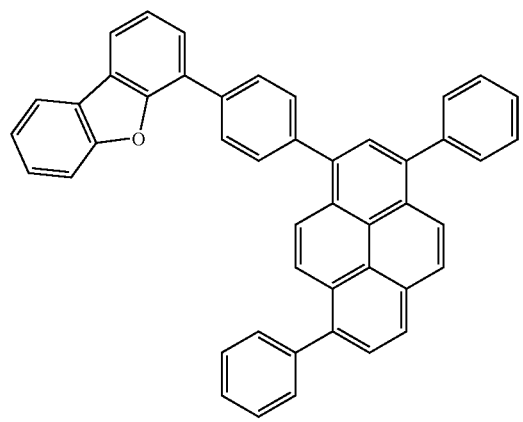
[90]
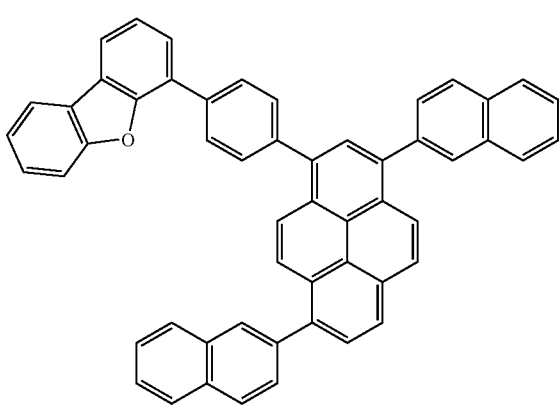
[88]
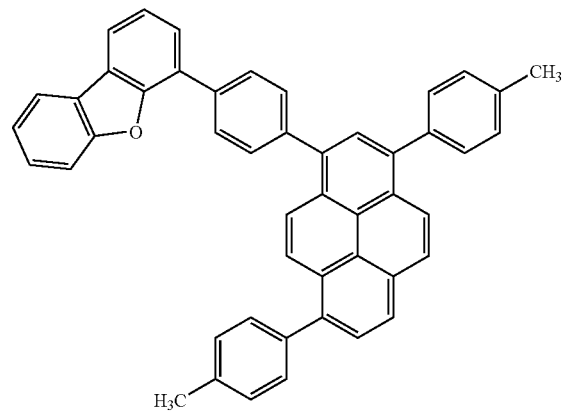
[91]

[Formula 11]
[92]
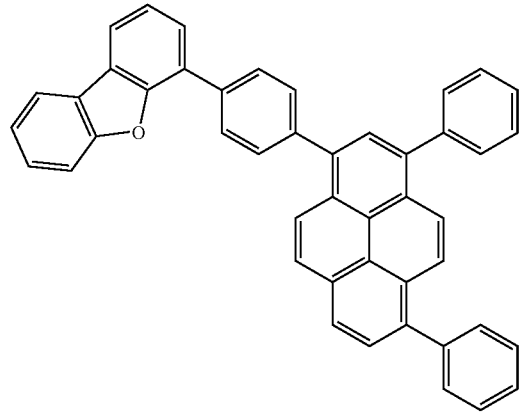
[93]
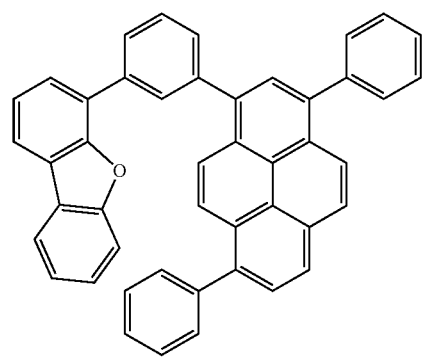
[94]
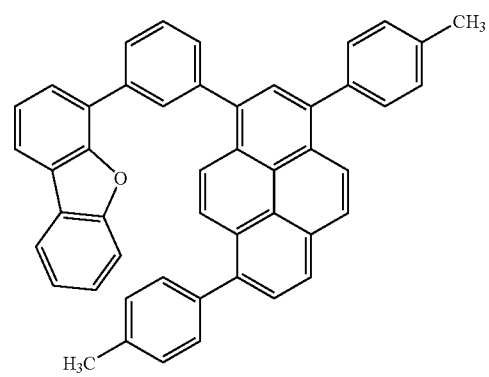
[95]
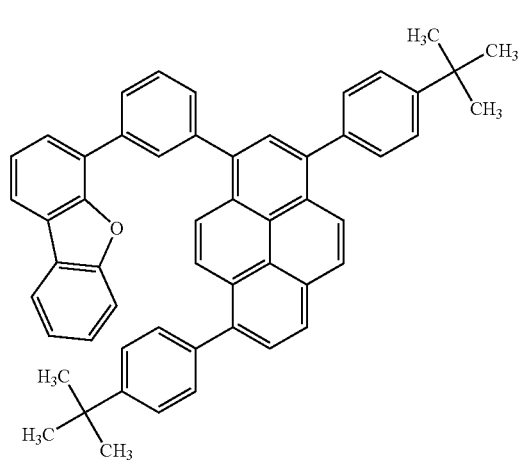
[96]
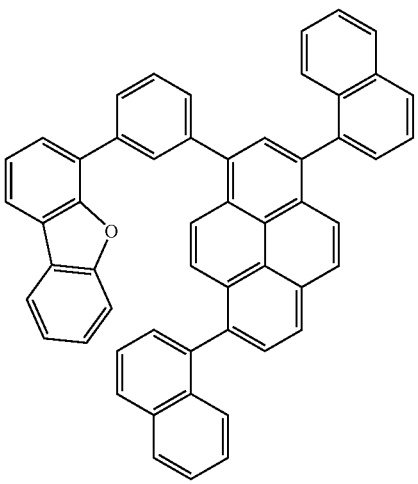
[97]
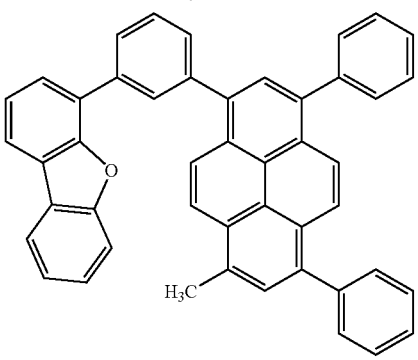
[98]
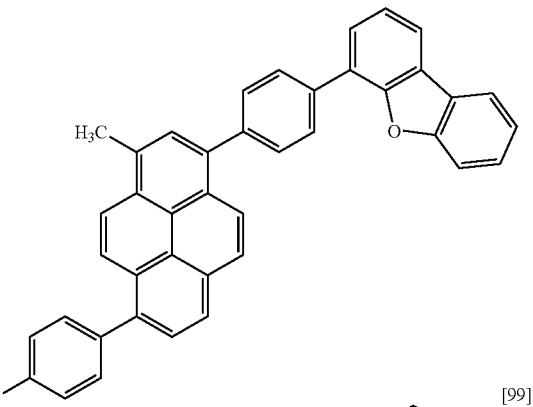
[99]
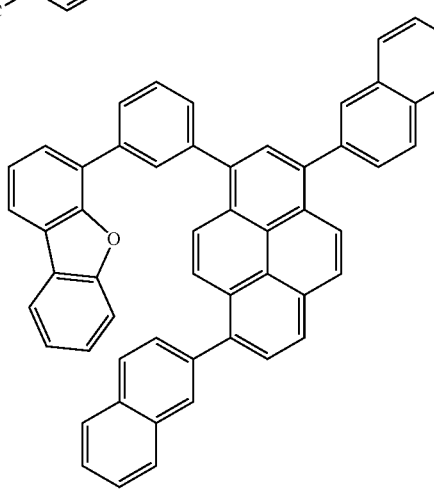

[Formula 12]
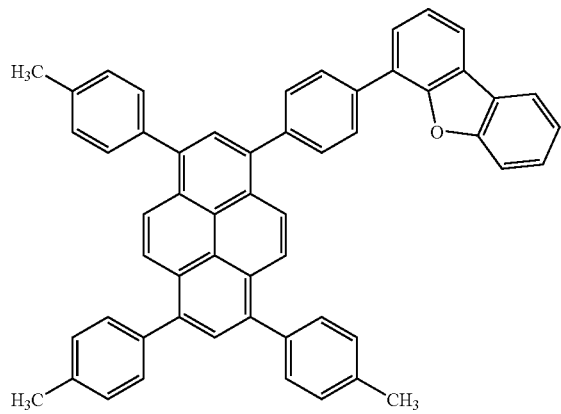
[100]
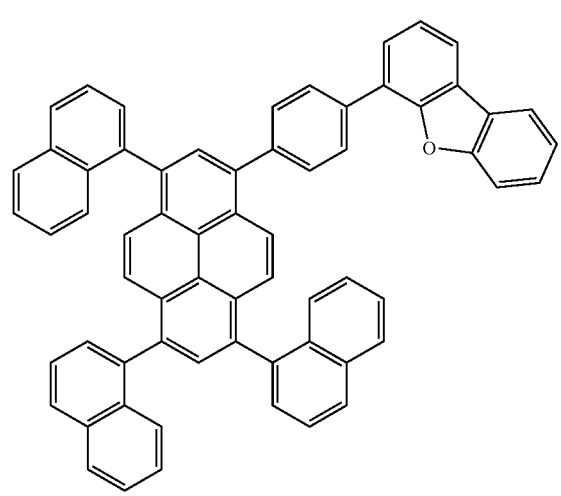
[101]
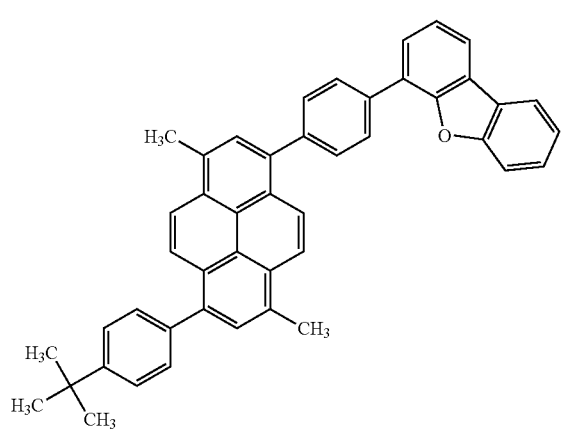
[102]
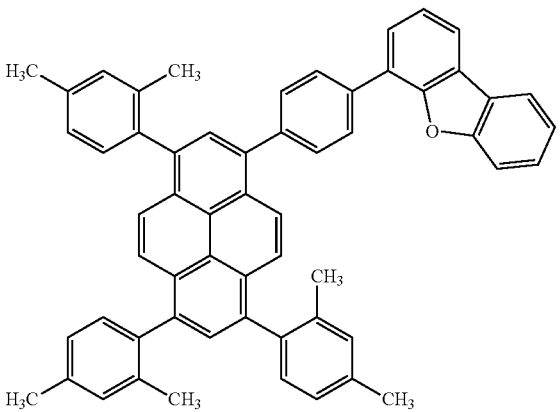
[103]
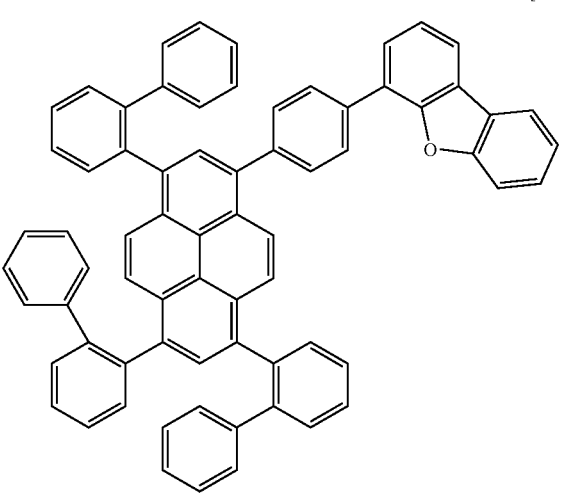
[104]
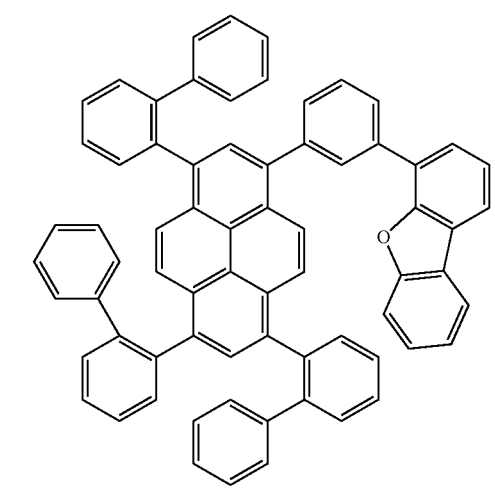
[105]

[106]
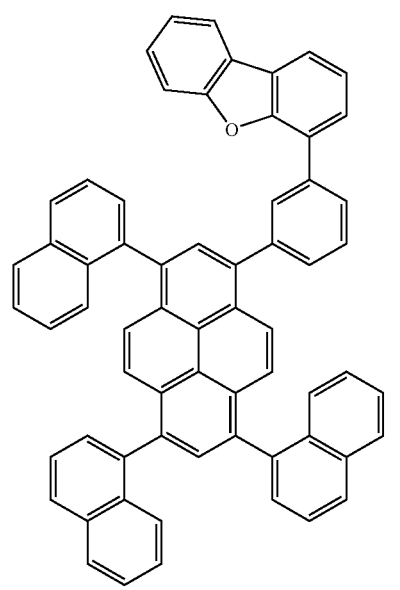
[107]
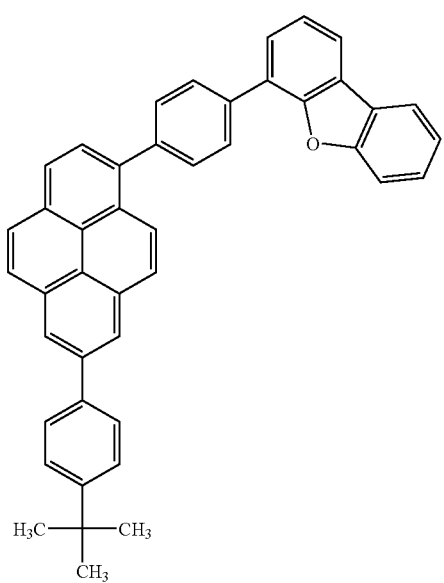
[108]
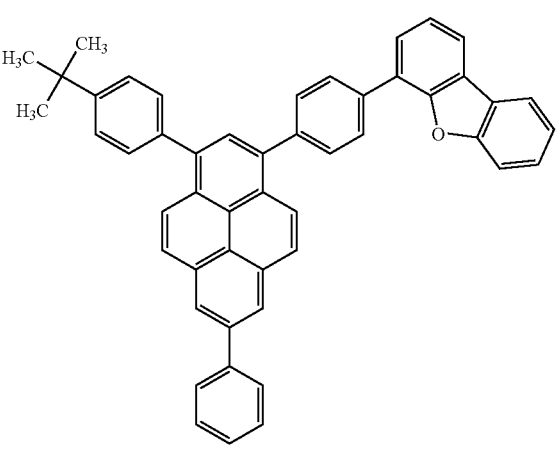
[109]
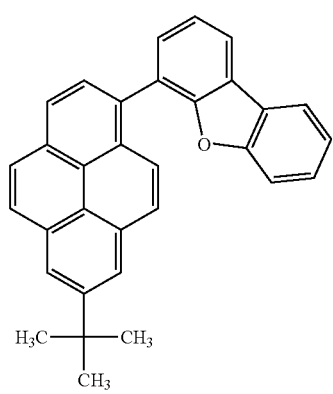
[110]
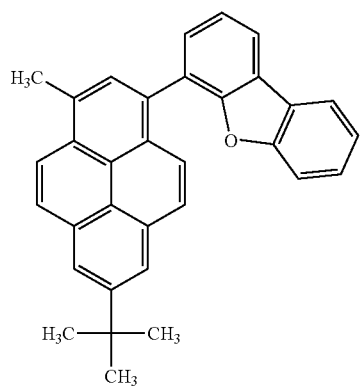
[111]
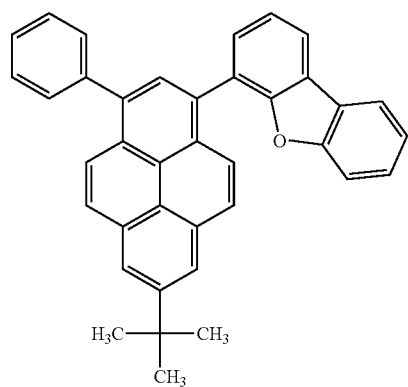
[112]
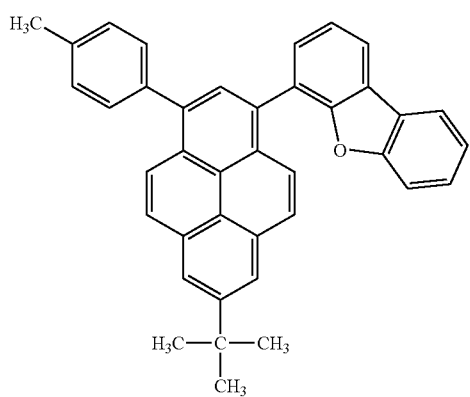

[Formula 13]
[113]
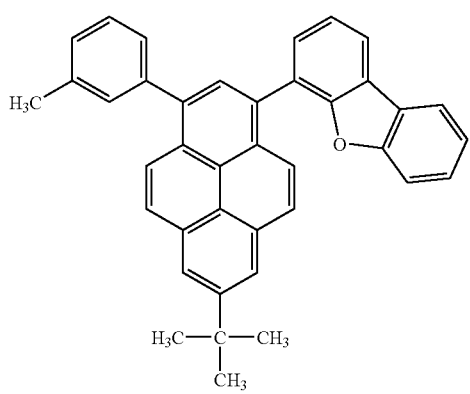
[114]
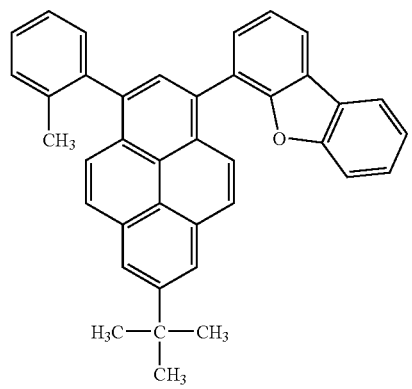
[115]
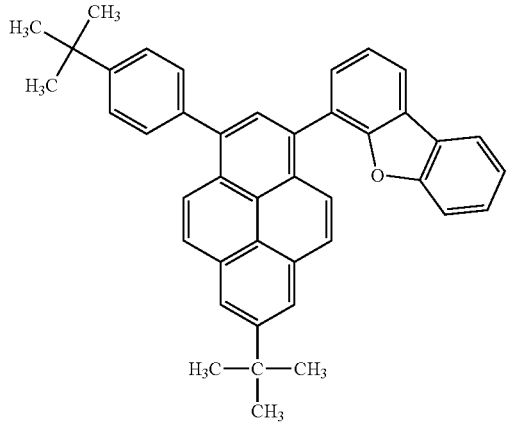
[116]
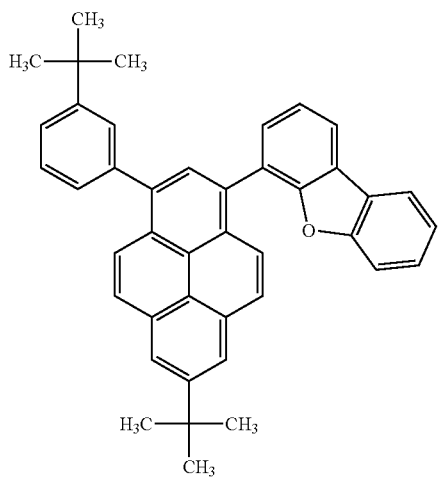
[117]
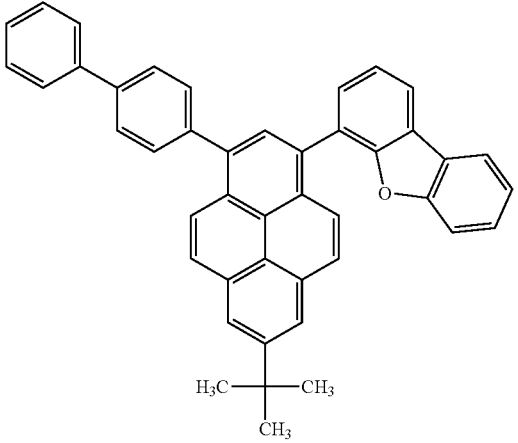
[118]
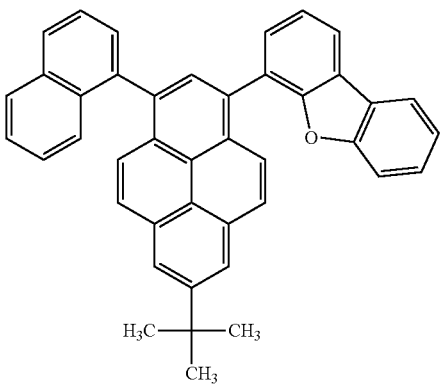

[119]
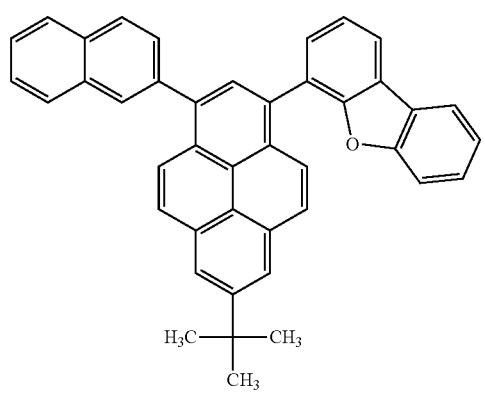
[120]
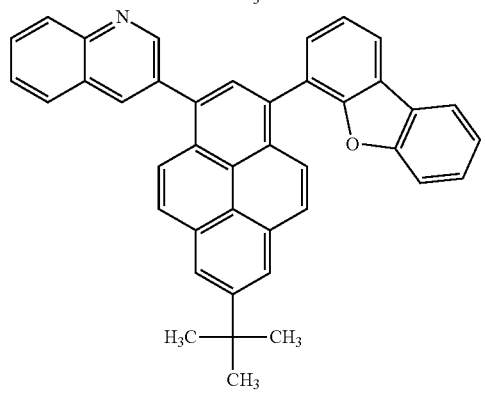
[121]
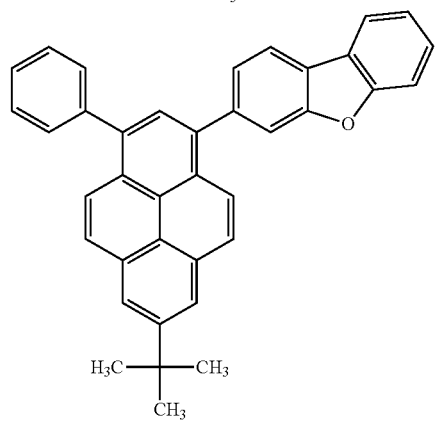
[122]
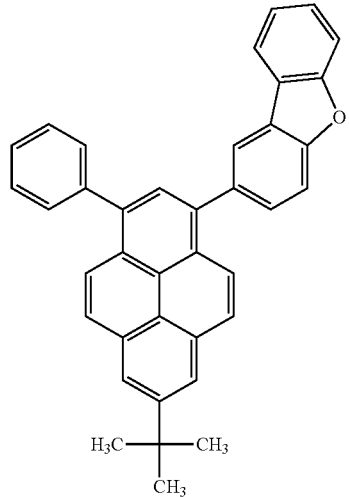
[123]
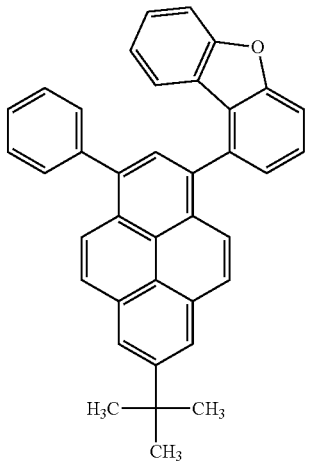
[124]
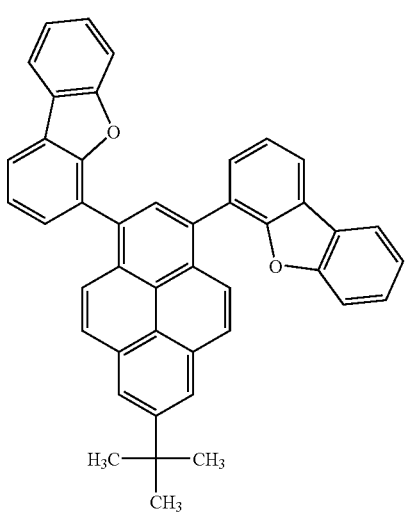
[Formula 14]
[125]
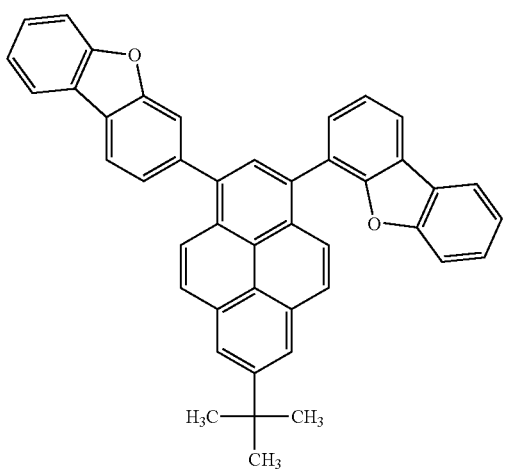

-continued
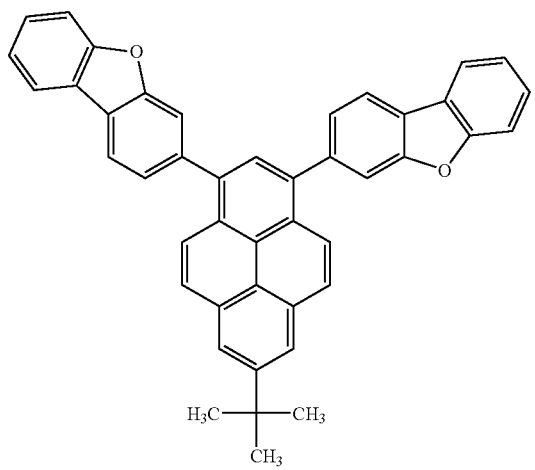
[126]
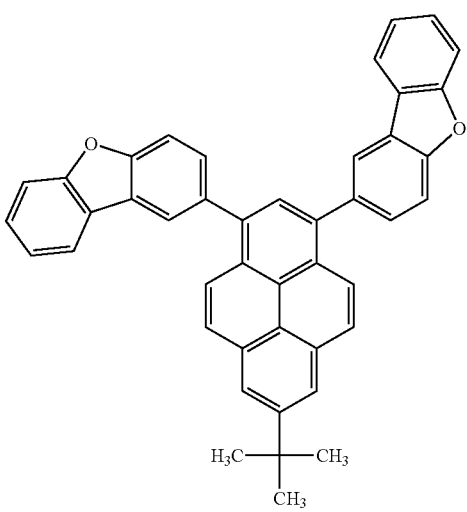
[129]
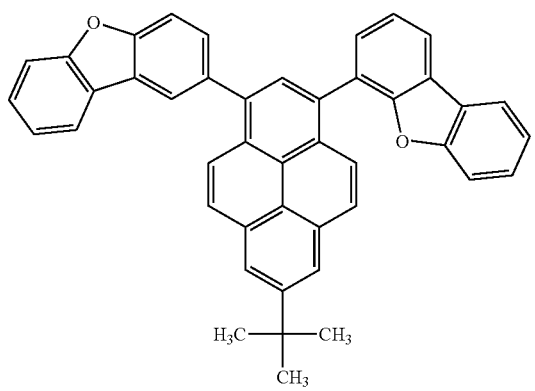
[127]
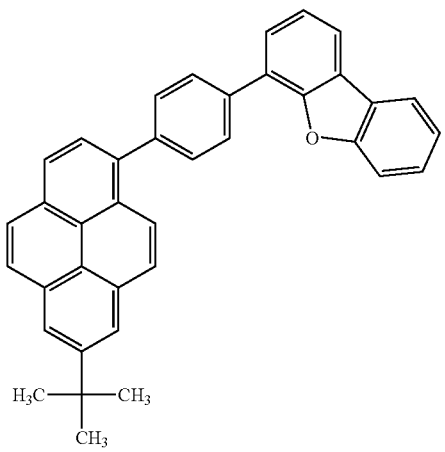
[130]
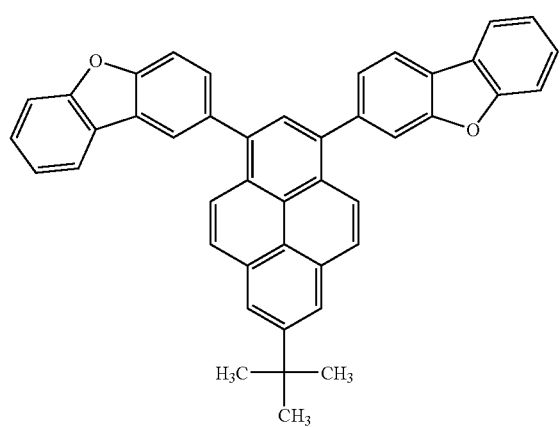
[128]
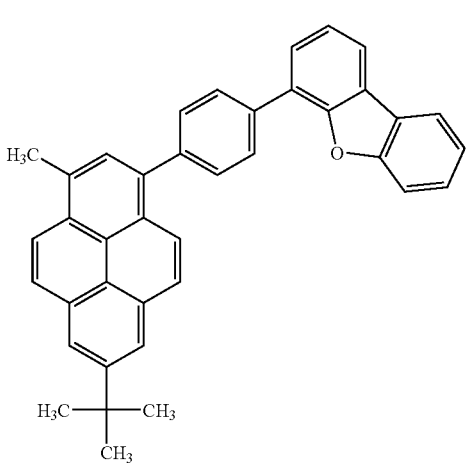
[131]

-continued
[132]
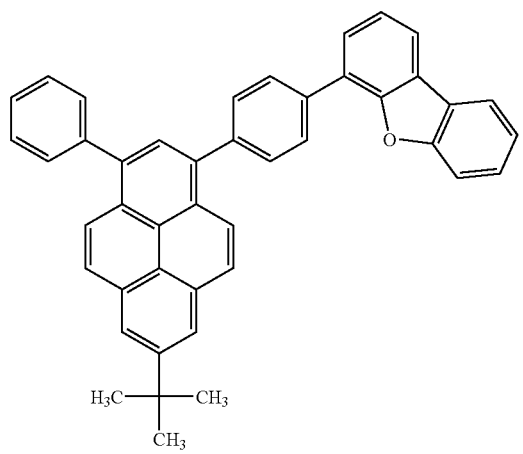
[133]
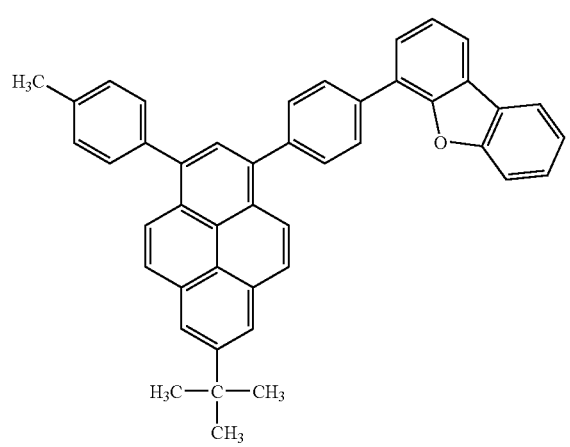
[134]
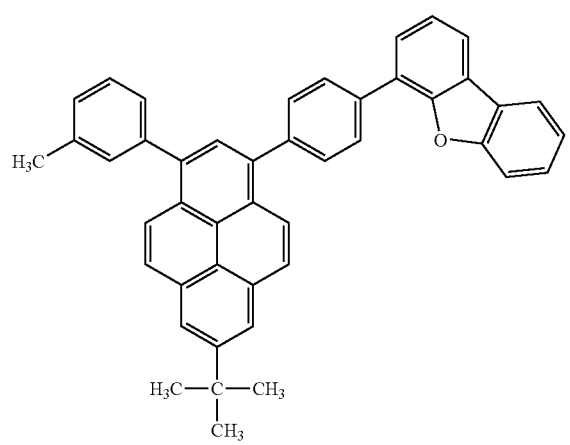
[Formula 15]
[135]
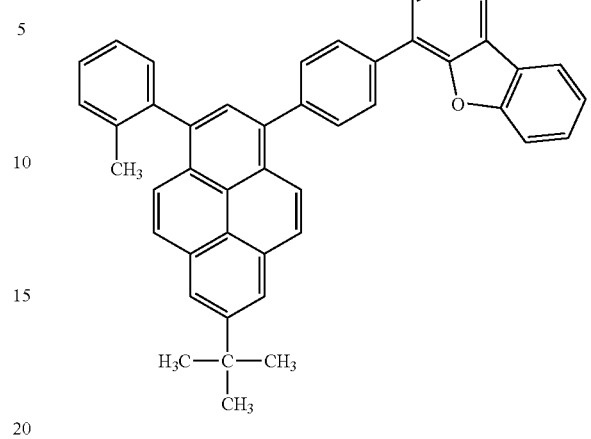
[136]
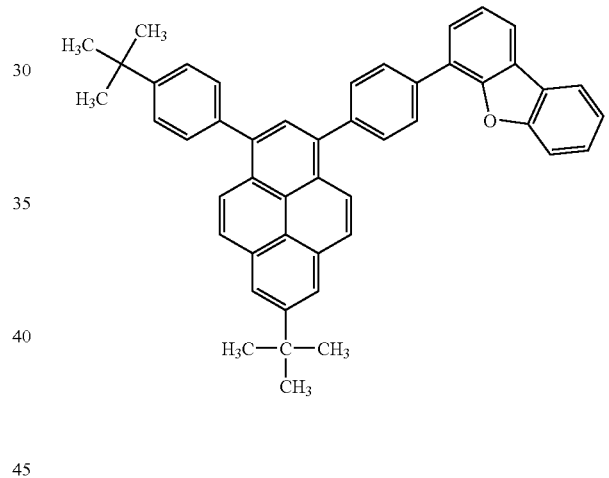
[137]
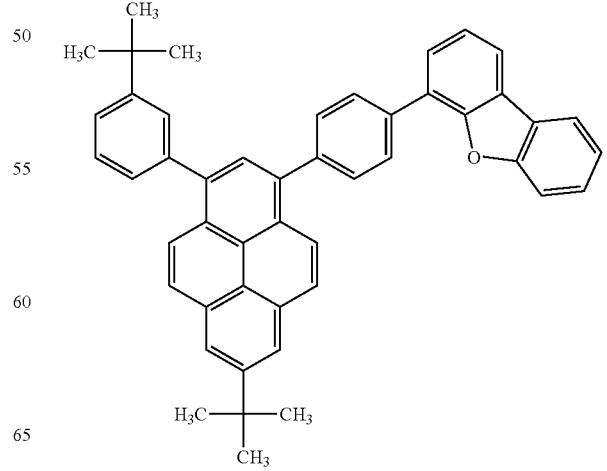

[138]
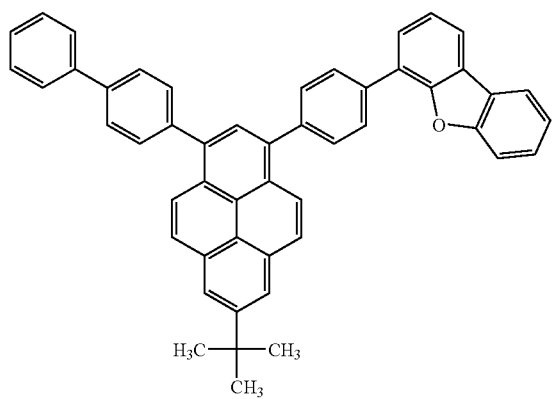
[141]
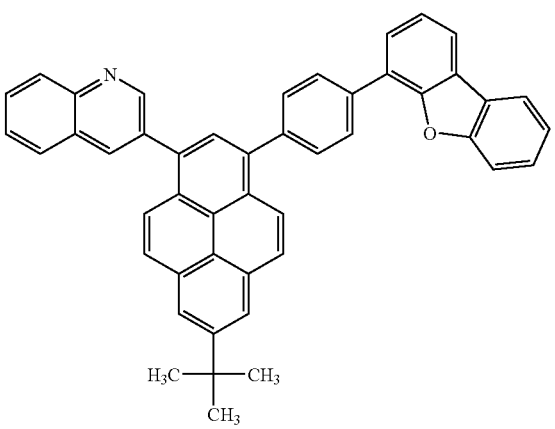
[139]
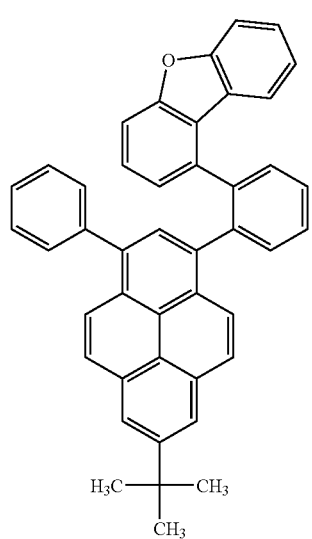
[142]
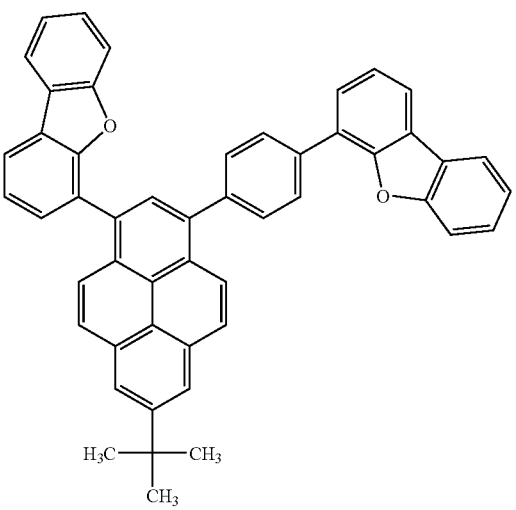
[140]
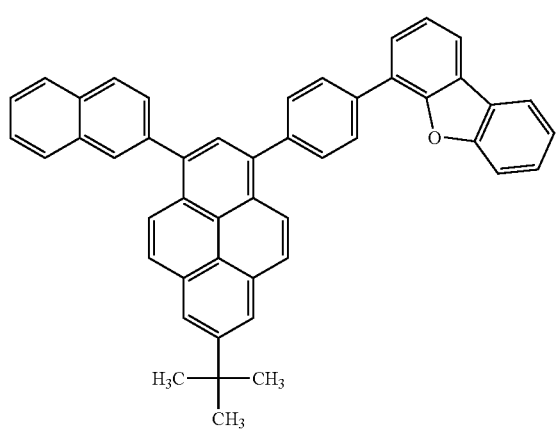
[143]
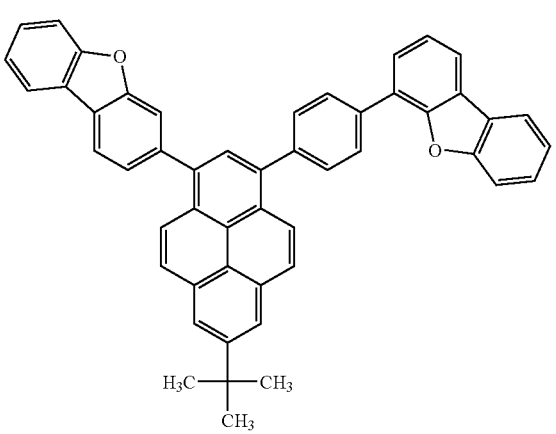

[144]
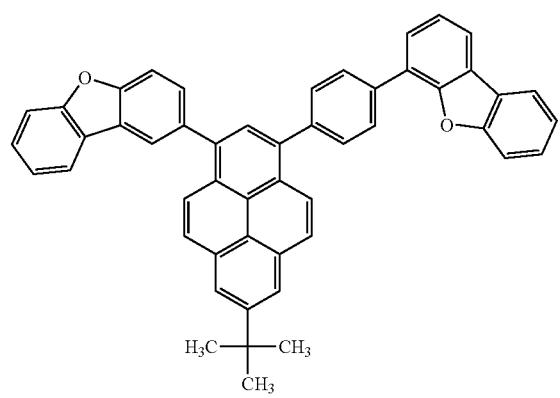
[147]
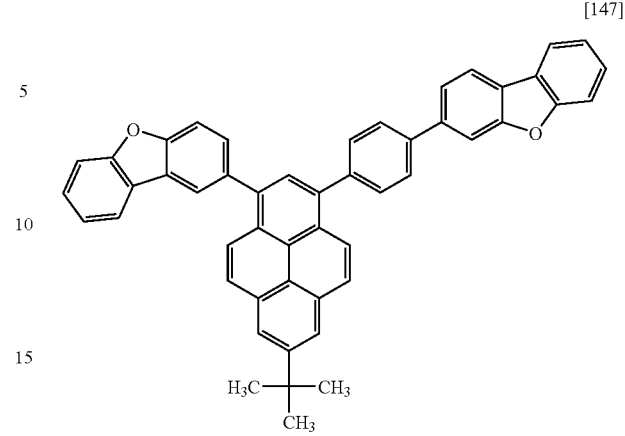
[Formula 16]
[145]
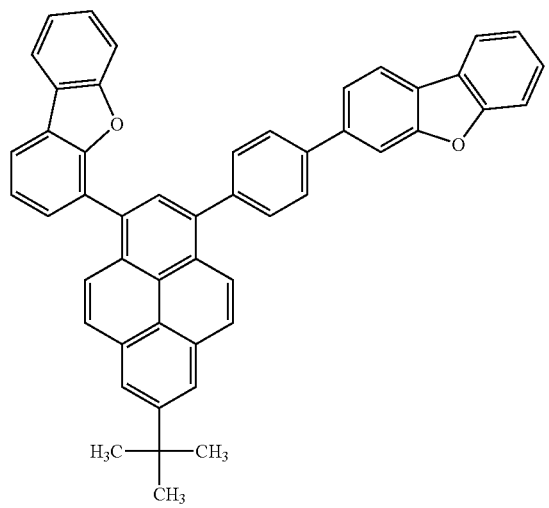
[148]
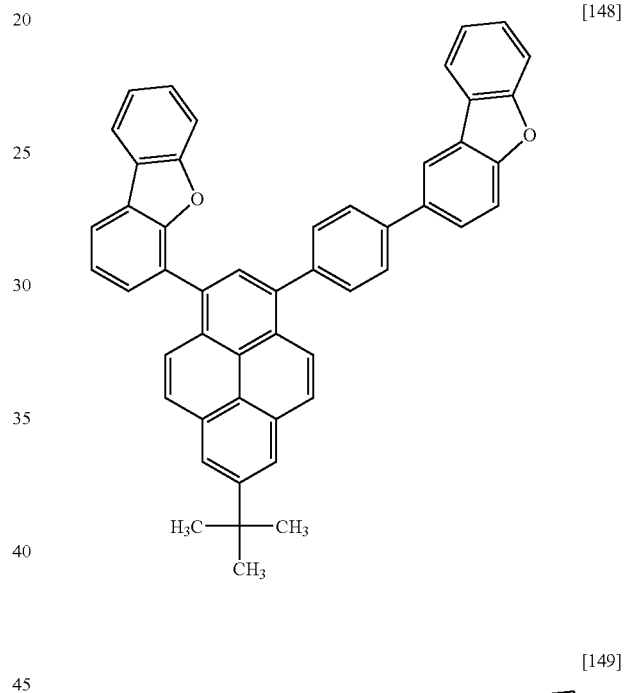
[146]
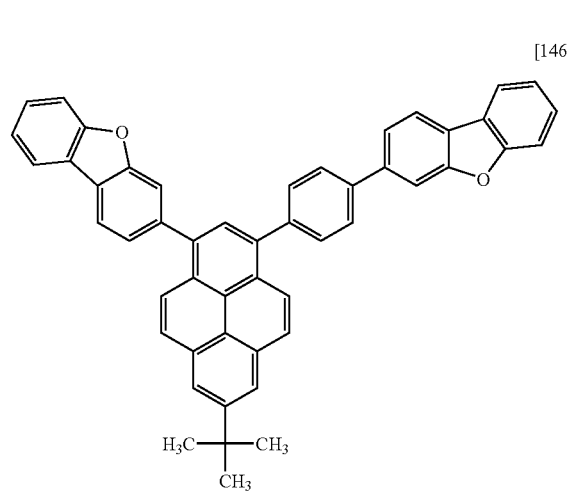
[149]
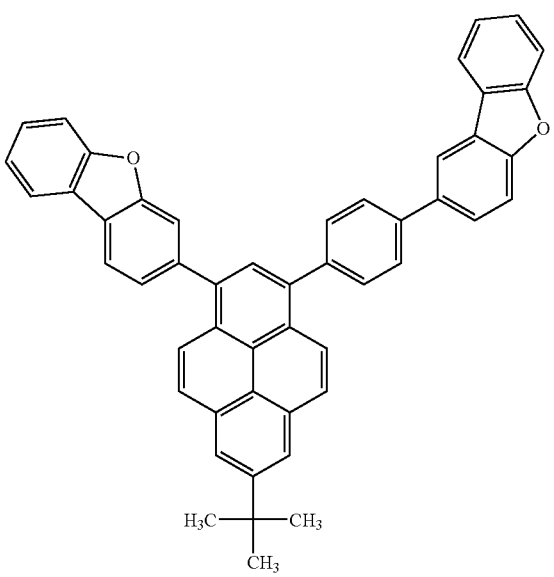

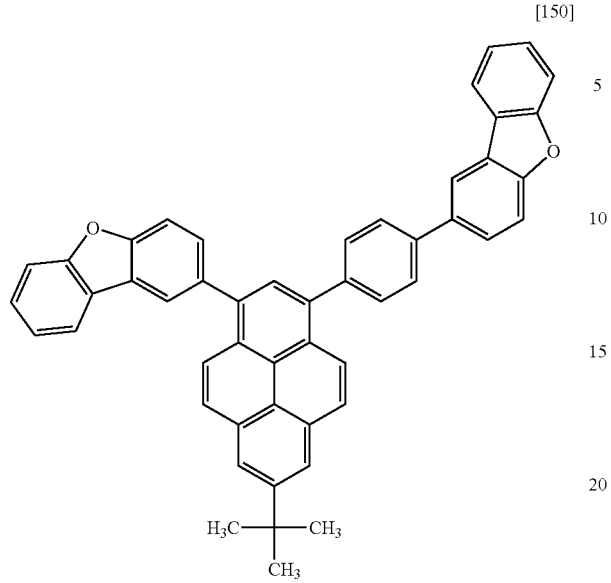
[150]
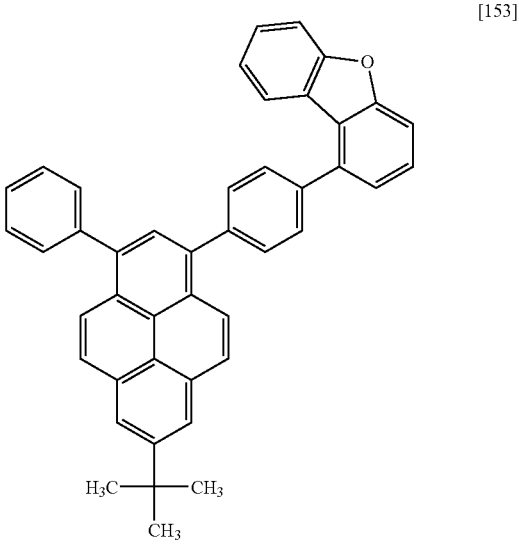
[153]
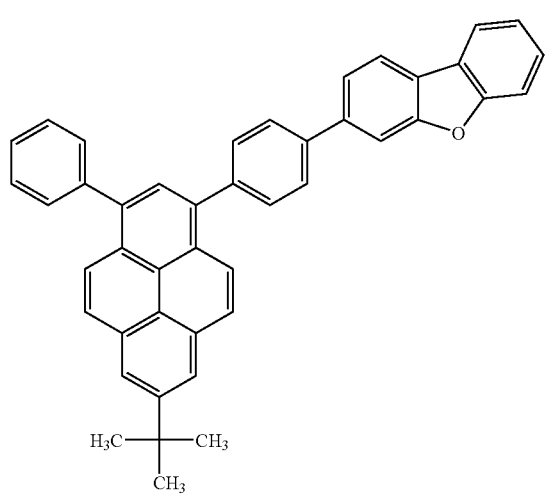
[151]
[Formula 17]
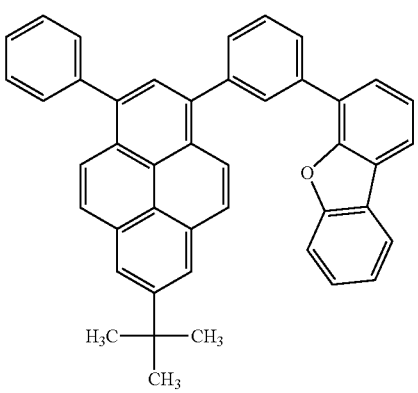
[154]
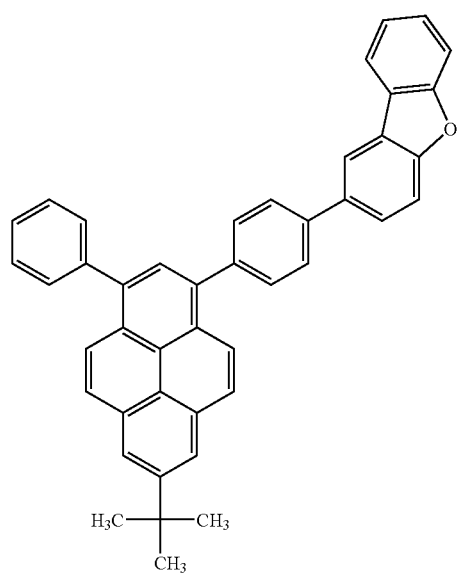
[152]

[156]
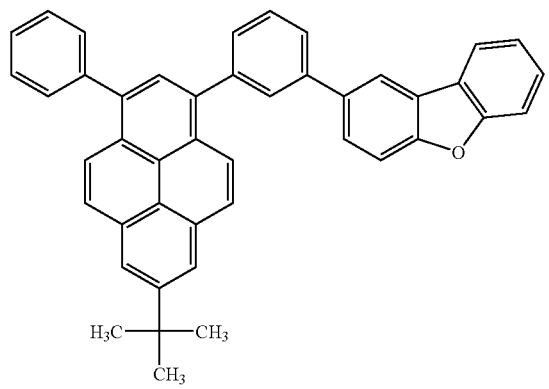
[157]
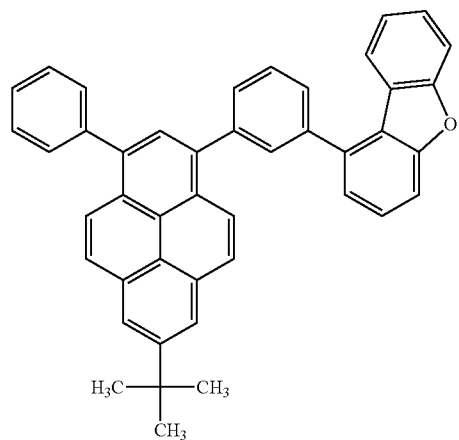
[158]
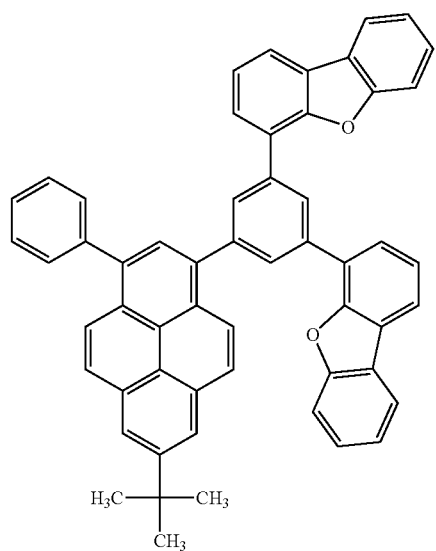
[159]
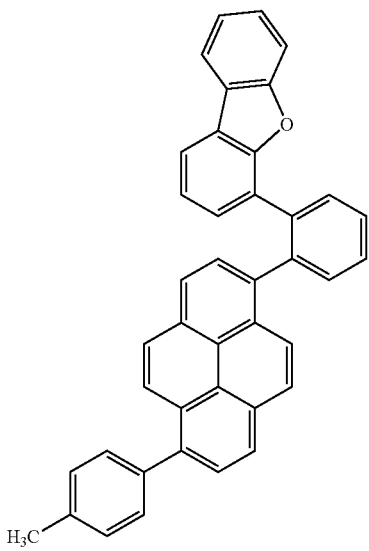
[160]
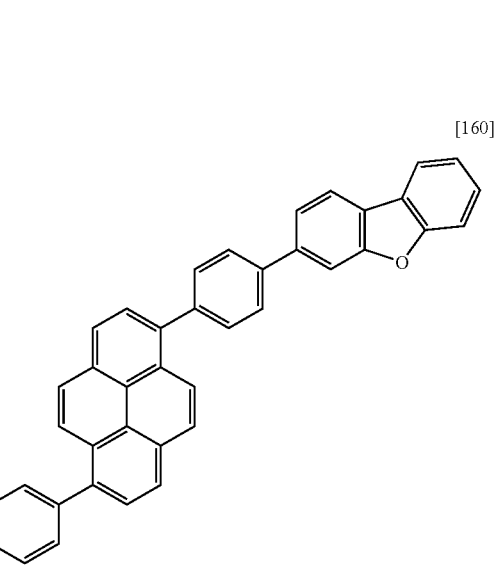
[161]
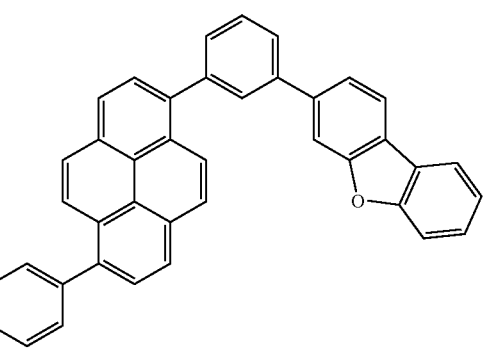

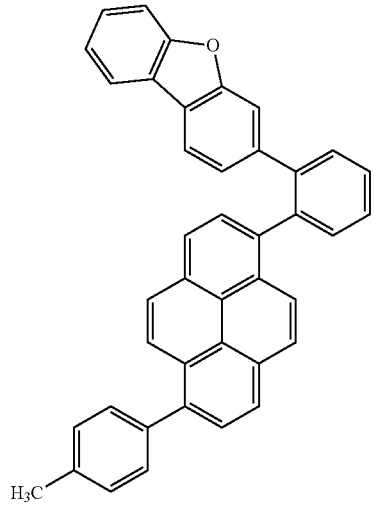
[162]
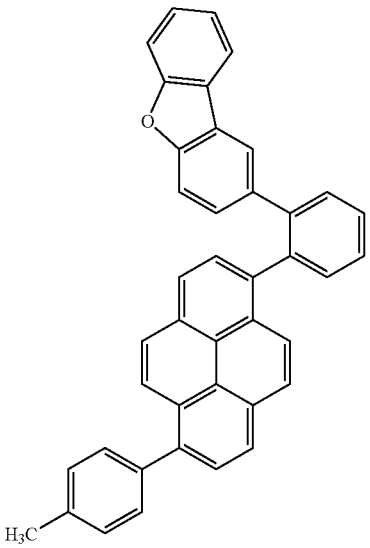
[165]
[Formula 18]
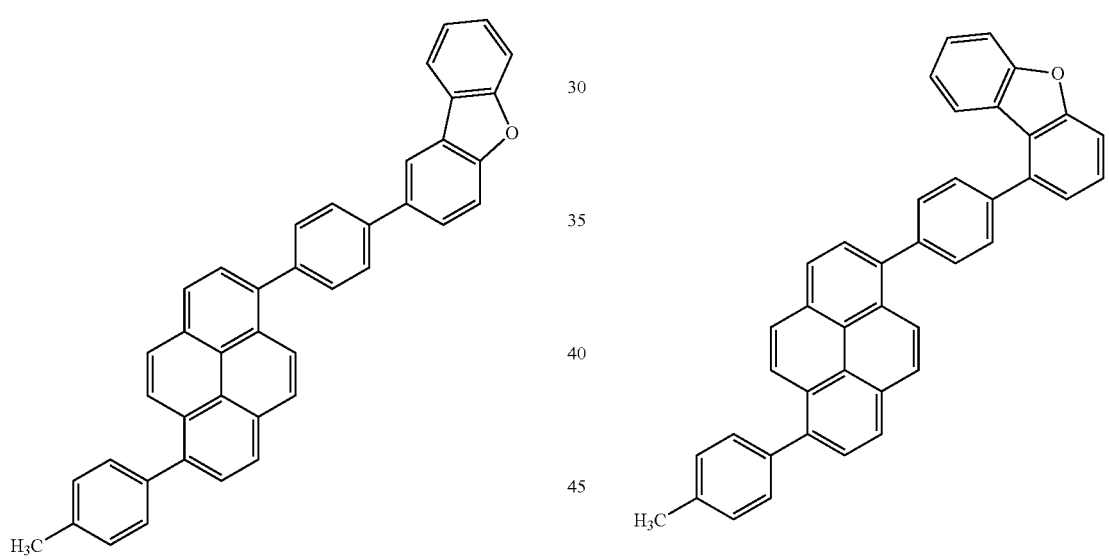
[163]
[166]
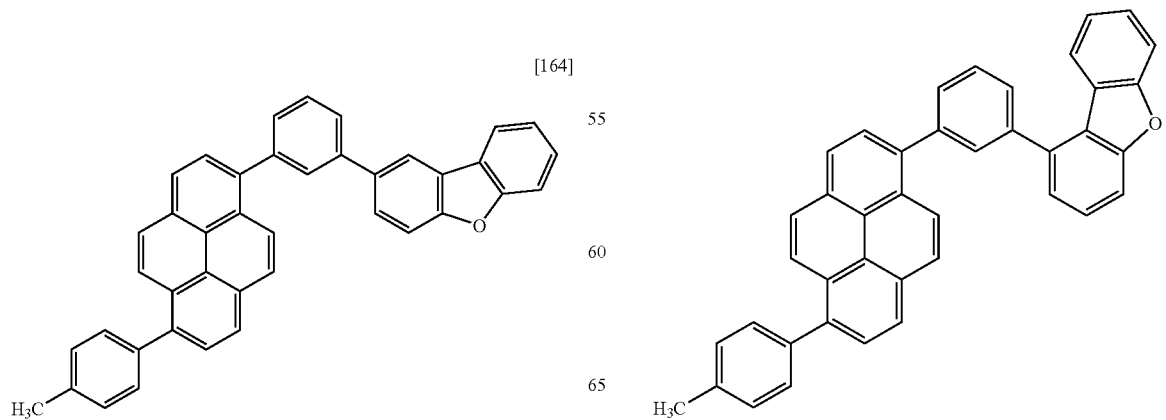
[164]
[167]

[168]
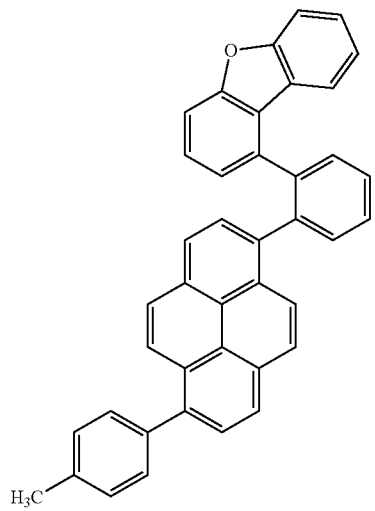
[169]
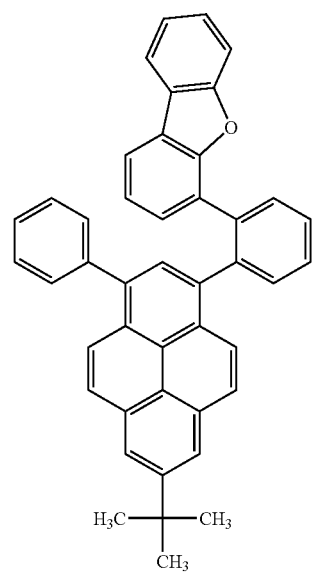
[170]
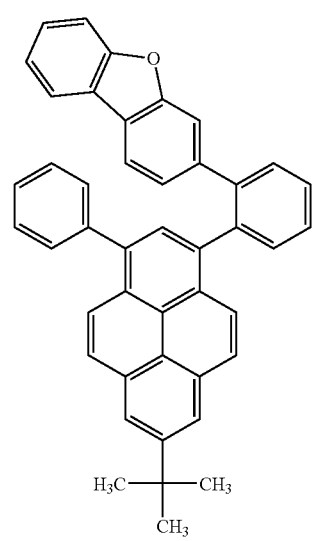
[171]
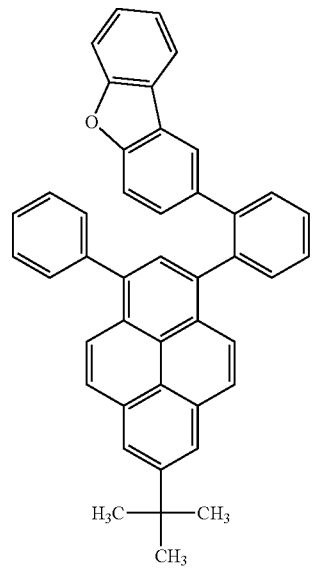
[172]
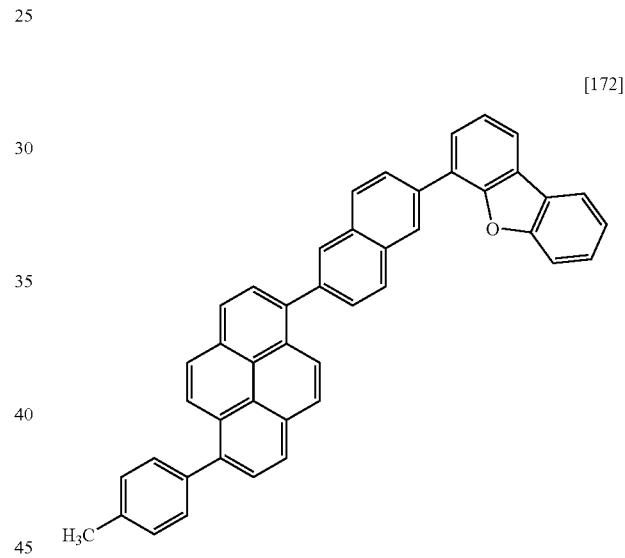
[173]
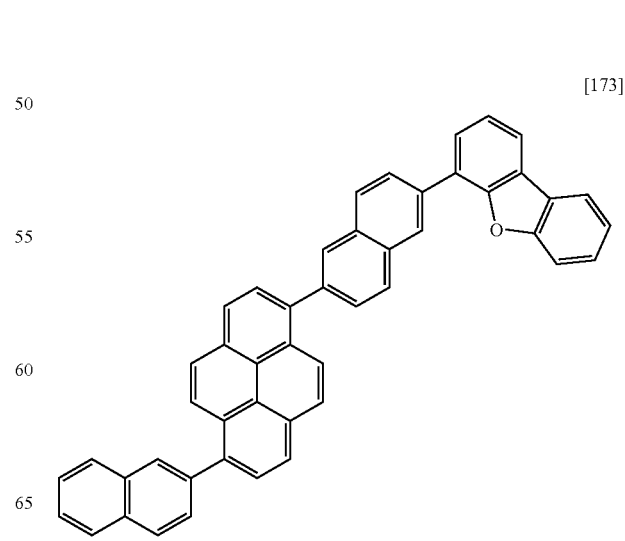

[174]
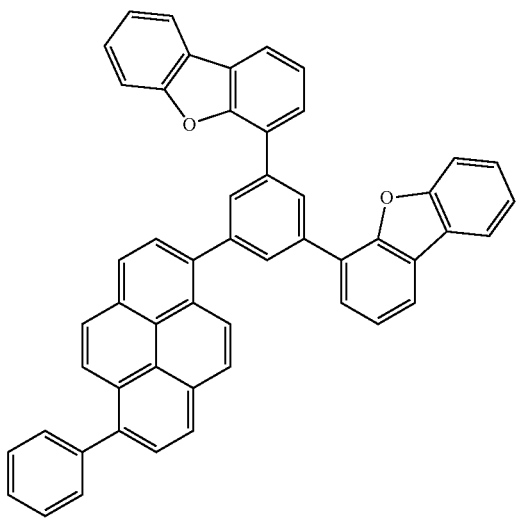
[175]
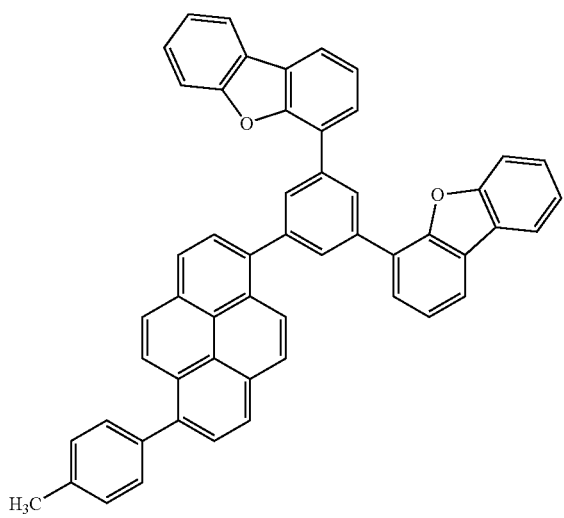
[176]
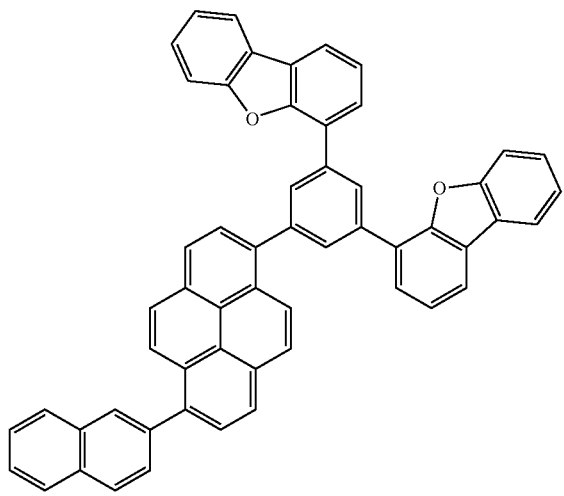
[177]
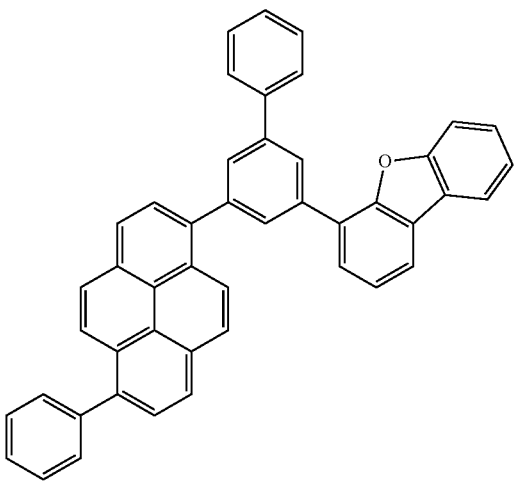
[178]
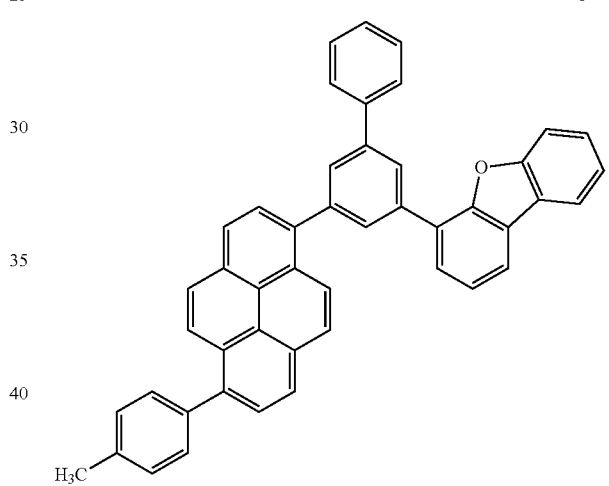
[179]
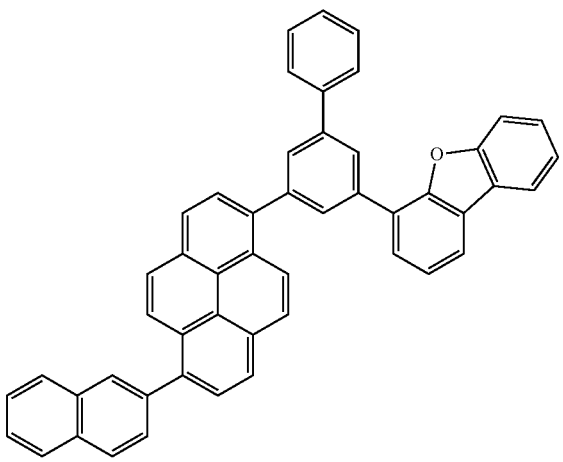

-continued

[Formula 19]

[180]

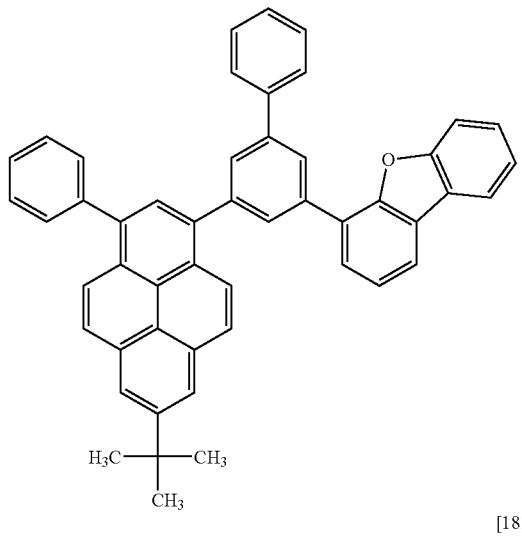

[181]

[182]

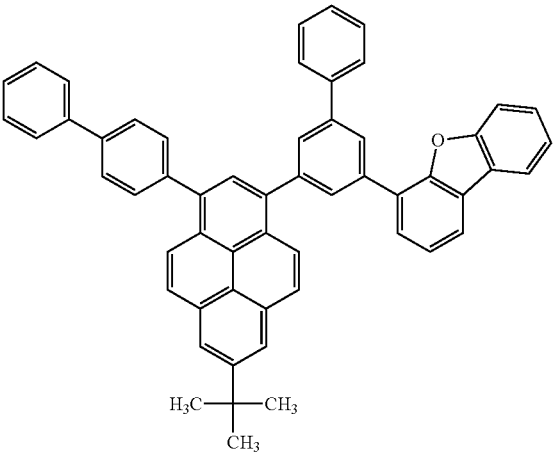

The pyrene compound represented by formula (1) may be synthesized using known methods. Examples of the method for introducing the dibenzofuranyl group into the pyrene skeleton include, but are not limited to, a method using a coupling reaction between a halogenated pyrene derivative and a dibenzofuran metal complex or a dibenzofuranyl aryl metal complex in the presence of a palladium or nickel catalyst and a method using a coupling reaction between a pyrenyl metal complex and a halogenated dibenzofuran derivative in the presence of a palladium or nickel catalyst.

Next, embodiments of the light emitting device according to the invention are described in detail by way of examples. The light emitting device of the invention includes an anode, a cathode and an organic layer interposed between the anode and the cathode, wherein the organic layer includes at least an emissive layer, and the emissive layer emits light using electric energy.

The organic layer may have a structure consisting of the emissive layer alone or may have a layered structure such as (1) a stack of hole transporting layer/emissive layer/electron transporting layer, (2) a stack of emissive layer/electron transporting layer or (3) a stack of hole transporting layer/emissive layer. Each layer may be a monolayer or multilayer. When the hole transporting layer and the electron transporting layer each have a plurality of layers, the layers in contact with the electrode may be called a "hole injection layer" and an "electron injection layer," respectively. It should be noted that in the description below, a hole injection material and an electron injection material belong to a hole transporting material and an electron transporting material, respectively.

In the light emitting device of an embodiment of the invention, the organic layer is made of a light emitting device material containing the pyrene compound represented by formula (1). The term "light emitting device material" refers to a compound contributable to light emission, which corresponds to either a self emissive material or an emission-assisting material. Examples of the light emitting device material include hole transporting materials, emissive materials and electron transporting materials.

The pyrene compound of the invention has high light-emitting performance and therefore is preferably used as an emissive material, while it may be used as a hole or electron transporting material. The pyrene compound of the invention exhibits strong emission in the blue color region and therefore is preferably used as a blue light emitting material, while it may be used in combination with any other emissive material to form a green to red light emitting device or a white light emitting device.

The anode used in an embodiment of the invention may be made of any material capable of efficiently injecting holes into the organic layer. A relatively high work-function material is preferably used to form the anode. Examples of such a material include electrically-conductive metal oxides such as tin oxide, indium oxide, indium zinc oxide, and indium tin oxide (ITO); metals such as gold, silver and chromium; inorganic electrically-conductive substances such as copper iodide and copper sulfide; and electrically-conductive polymers such as polythiophene, polypyrrole and polyaniline. One or more of these electrode materials may be used alone or in a layered or mixed manner.

The anode may have a resistance such that a sufficient current can be supplied for the light emission of the light emitting device and preferably has a low resistance in view of the power consumption of the light emitting device. For example, an ITO substrate with a resistance of 300 Ω/square or less can function as a device electrode. At present, a substrate with a resistance of about 10 Ω/square is also available, and therefore, using a low resistance material with a resistance of 100 Ω/square or less is particularly preferred. The thickness of the ITO electrode is generally from 100 to 300 nm, while it may be freely selected depending on the resistance value.

The light emitting device is preferably formed on a substrate in order to maintain its mechanical strength. The substrate is preferably a glass substrate such as a soda glass or non-alkali glass substrate. The glass substrate only has to have a thickness sufficient for the maintenance of the mechanical strength. Therefore, a thickness of at least 0.5 mm will be enough. The glass preferably has such quality that the amount of ions leached from the glass is as small as possible. Therefore, the glass is preferably non-alkali glass. A soda-lime glass material having a barrier coating such as a $SiO_2$ coating is also commercially available, and such a glass material may also be used. When the anode functions stably, the substrate does not have to be made of glass, and, for example, the anode may be formed on a plastic substrate. Methods for forming the ITO film include, but are not limited to, electron beam methods, sputtering methods and chemical reaction methods.

In an embodiment of the invention, any material capable of efficiently injecting electrons into the organic layer may be used for the cathode. Examples of such a material generally include platinum, gold, silver, copper, iron, tin, zinc, aluminum, indium, chromium, lithium, sodium, potassium, cesium, calcium, and magnesium, and alloys thereof. Lithium, sodium, potassium, cesium, calcium, magnesium, or an alloy containing any of such low work-function metals is effective in increasing the electron injection efficiency and improving the device characteristics. However, such low work-function metals are often generally unstable in the air. In a preferred method, therefore, a small amount of lithium or magnesium (1 nm or less as indicated by a film thickness meter for vacuum deposition) may be doped on the organic layer to form a highly stable electrode. An inorganic salt such as lithium fluoride may also be used. In a preferred example, a metal such as platinum, gold, silver, copper, iron, tin, aluminum, or indium, or an alloy of any of these metals, an inorganic material such as silica, titania or silicon nitride, or an organic polymer compound such as polyvinyl alcohol, polyvinyl chloride or a hydrocarbon polymer compound may also be deposited to protect the electrode. Any method capable of ensuring conductivity, such as resistance heating evaporation, electron beam application, sputtering, ion plating, or coating, may be used to form these electrodes.

The hole transporting layer may be formed by a method of laminating or mixing one or more hole transporting materials or a method using a mixture of a hole transporting material and a polymer binder. An inorganic salt such as iron (III) chloride may be added to the hole transporting material in the process of forming the hole transporting layer. Any compound capable of forming a thin film necessary for the preparation of the light emitting device, allowing holes to be injected from the anode, and transporting holes may be used as the hole transporting material. Preferred examples of the hole transporting material include triphenylamine derivatives such as 4,4'-bis(N-(3-methylphenyl)-N-phenylamino)biphenyl, 4,4'-bis(N-(1-naphthyl)-N-phenylamino)biphenyl and 4,4',4"-tris(3-methylphenyl(phenyl)amino)triphenylamine; biscarbazole derivatives such as bis(N-allylcarbazole) and bis(N-alkylcarbazole); pyrazoline derivatives; stilbene compounds; hydrazone compounds; heterocyclic compounds such as benzofuran derivatives, thiophene derivatives, oxadiazole derivatives, phthalocyanine derivatives, and porphyrin derivatives; and polymer materials such as styrene derivatives and polycarbonates having any of the above monomers in the side chain, polythiophene, polyaniline, polyfluorene, polyvinylcarbazole, and polysilane.

In an embodiment of the invention, the emissive layer may be any of a monolayer and a multilayer, each of which is made of an emissive material (a host material, a dopant material) which may be a host material alone or a mixture of a host material and a dopant material. In each emissive layer of the light emitting device of the invention, therefore, only the host material or the dopant material may emit light, or both the host material and the dopant material may emit light. In order to efficiently use electric energy and produce high-color-purity light emission, the emissive layer preferably includes a mixture of the host material and the dopant material. The host material and the dopant material may each be a single type or a combination of different types. The dopant material may be entirely or partially contained in the host material. The dopant material may be deposited to form a layer or dispersed. The dopant material is preferably used in an amount of 20% by weight or less, more preferably 10% by weight or less, based on the amount of the host material, because if the amount is too large, concentration quenching may occur. In the doping method, co-evaporation of the host material and the dopant material may be performed to form the layer. Alternatively, the dopant material may be premixed with the host material, and then the mixture may be vapor-deposited.

In an embodiment of the invention, the emissive layer includes the pyrene compound represented by formula (I). In an embodiment of the invention, the pyrene compound has a high level of thin-film stability and charge transporting performance and therefore is preferably used as a host material, while it may be used as a dopant material.

The ionization potential of the pyrene compound represented by formula (1) of the invention is preferably, but not limited to, from 4.6 eV to 6.2 eV, more preferably from 4.8 eV to 6.0 eV. In an embodiment of the invention, the ionization potential may be a value obtained by measuring a 30 to 100 nm-thick vapor-deposited thin film on an ITO glass substrate with an atmospheric ultraviolet photoelectron analyzer (AC-1, manufactured by RIKENKIKI CO., LTD), while the absolute value of the ionization potential may depend on the measurement method.

The host material for use in an embodiment of the invention is not limited to only one type of the pyrene compound represented by formula (1). Different types of the pyrene compounds according to embodiments of the invention may be used to form a mixture, or one or more other host materials may be used in combination with the pyrene compound according to embodiments of the invention. Examples of host materials that may preferably be used in combination with the pyrene compound include condensed aryl ring-containing compounds such as anthracene, and derivatives thereof; aromatic amine derivatives such as N,N'-dinaphthyl-N,N'-diphenyl-4,4'-diphenyl-1,1'-diamine; metal-chelated oxynoid compounds such as tris(8-quinolinato)aluminum (III); bis-styryl derivatives such as distyrylbenzene derivatives; tetraphenylbutadiene derivatives; indene derivatives; coumarin derivatives; oxadiazole derivatives; pyrrolopyridine derivatives; perinone derivatives; cyclopentadiene derivatives; oxadiazole derivatives; carbazole derivatives; pyrrolopyrrole derivatives; and polymer host materials such as polyphenylenevinylene derivatives, polyparaphenylene derivatives, polyfluorene derivatives, polyvinylcarbazole derivatives, and polythiophene derivatives.

Examples of the dopant material include, but are not limited to, condensed aryl ring-containing compounds such as naphthalene, anthracene, phenanthrene, pyrene, triphenylene, perylene, fluorene, and indene, and derivatives thereof (e.g., 2-(benzothiazol-2-yl)-9,10-diphenylanthracene and 5,6,11,12-tetraphenylnaphthacene); heteroaryl ring-containing compounds such as furan, pyrrole, thiophene, silole, 9-silafluorene, 9,9'-spirobisilafluorene, benzothiophene, benzofuran, indole, dibenzothiophene, dibenzofuran, imidazopyridine, phenanthroline, pyrazine, naphthyridine, quinoxaline, pyrrolopyridine, and thioxanthene, and derivatives thereof; borane derivatives; distyrylbenzene derivatives; aminostyryl derivatives such as 4,4'-bis(2-(4-diphenylaminophenyl)ethenyl)biphenyl and 4,4'-bis(N-(stilben-4-yl)-N-phenylamino)stilbene; aromatic acetylene derivatives; tetraphenylbutadiene derivatives; stilbene derivatives; aldazine derivatives; pyrromethene derivatives; diketopyrrolo[3,4-c]pyrrole derivatives; coumarin derivatives such as 2,3,5,6-1H,4H-tetrahydro-9-(2'-benzothiazolyl)quinolidino[9,9a,1-gh]coumarin; azole derivatives such as imidazole, thiazole, thiadiazole, carbazole, oxazole, oxadiazole, and triazole, and metal complexes thereof; and aromatic amine derivatives such as N,N'-diphenyl-N,N'-di(3-methylphenyl)-4,4'-diphenyl-1,1'-diamine. In particular, a condensed aromatic ring derivative having an electron-accepting substituent is preferably used as a dopant, so that the thin-film stability effect of the pyrene compound can become more significant. Examples of such a particularly preferred dopant include benzazol group-containing pyrene compounds such as 1-(benzoxazol-2-yl)-3,8-bis(4-methylphenyl)pyrene and dimesitylboryl group-containing pyrene compounds such as (6-p-tolylpyrene-1-yl)-bis(2,4,6-trimethylphenyl)borane.

In an embodiment of the invention, the electron transporting layer is a layer into which electrons are injected from a cathode and which transports electrons. The electron transporting layer should have high electron injection efficiency and the ability to efficiently transport the injected electrons. Therefore, the electron transporting layer is preferably made of a substance that has a high level of electron affinity, electron mobility and stability and is less likely to cause trapping impurities during the manufacturing process and use. In view of a balance between hole transportation and electron transportation, however, the electron transporting layer may be made of a material whose electron transporting performance is not so high, because if the electron transporting layer mainly plays a role in efficiently blocking the flow of unrecombined holes from the anode to the cathode, the electron transporting layer made of the material whose electron transporting performance is not so high can produce substantially the same luminance efficiency-increasing effect as in the case where the electron transporting layer is made of a material having high electron transporting performance. In an embodiment of the invention, therefore, a hole blocking layer capable of efficiently blocking hole transfer has the same meaning as the electron transporting layer and is encompassed by the electron transporting layer.

Examples of electron transporting materials for use in the electron transporting layer include, but are not limited to, condensed aryl ring-containing compounds such as naphthalene and anthracene, and derivatives thereof; styryl aromatic ring derivatives such as 4,4'-bis(diphenylethenyl)biphenyl; perylene derivatives; perinone derivatives; coumarin derivatives; naphthalimide derivatives; quinone derivatives such as anthraquinone and diphenoquinone; phosphorus oxide derivatives; carbazole derivatives and indole derivatives; quinolinol complexes such as tris(8-quinolinolato)aluminum (III); hydroxyazole complexes such as hydroxyphenyloxazole complexes; azomethine complexes; tropolone metal complexes; and flavonol metal complexes. In particular, a compound having an electron-accepting nitrogen-containing heteroaryl ring structure and including at least one constituent element selected from carbon, hydrogen, nitrogen, oxygen, silicon, and phosphorus is preferably used, because such a compound can reduce the driving voltage.

As used herein, the term "electron-accepting nitrogen" refers to a nitrogen atom that forms a multiple bond together with an adjacent atom. Since the nitrogen atom has high electro-negativity, the multiple bond has electron-accepting properties. Therefore, the electron-accepting nitrogen-containing heteroaryl ring has high electron affinity and good electron transporting performance, so that it can reduce the driving voltage of the light emitting device when used in the electron transporting layer. Examples of the electron-accepting nitrogen-containing heteroaryl ring include a pyridine ring, a pyrazine ring, a pyrimidine ring, a quinoline ring, a quinoxaline ring, a naphthyridine ring, a pyrimidopyrimidine ring, a benzoquinoline ring, a phenanthroline ring, an imidazole ring, an oxazole ring, an oxadiazole ring, a triazole ring, a thiazole ring, a thiadiazole ring, a benzoxazole ring, a benzothiazole ring, a benzimidazole ring, and a phenanthroimidazole ring.

Preferable examples of such heteroaryl ring structure-containing compounds include benzimidazole derivatives, benzoxazole derivatives, benzothiazole derivatives, oxadiazole derivatives, thiadiazole derivatives, triazole derivatives, pyrazine derivatives, phenanthroline derivatives, quinoxaline derivatives, quinoline derivatives, benzoquinoline derivatives, oligopyridine derivatives such as bipyridine and terpyridine, quinoxaline derivatives, and naphthyridine derivatives. In particular, examples that are preferably used in view of electron transporting performance include imidazole derivatives such as tris(N-phenylbenzimidazol-2-yl)benzene, oxadiazole derivatives such as 1,3-bis[(4-tert-butylphenyl)1,3,4-oxadiazolyl]phenylene, triazole derivatives such as N-naphthyl-2,5-diphenyl-1,3,4-triazole, phenanthroline derivatives such as bathocuproine and 1,3-bis(1,10-phenanthrolin-9-yl)benzene, benzoquinoline derivatives such as 2,2'-bis(benzo[h]quinolin-2-yl)-9,9'-spirobifluorene, bipyridine derivatives such as 2,5-bis(6'-(2',2"-bipyridyl))-1,1-dimethyl-3,4-diphenylsilole, terpyridine derivatives such as 1,3-bis(4'-(2,2':6'2"-terpyridinyl))benzene, and naphthyridine derivatives such as bis(1-naphthyl)-4-(1,8-naphthyridin-2-yl)phenylphosphine oxide.

The above electron transporting materials may be used alone, or two or more of the above electron transporting materials may be used to form a mixture. In addition, any of the above electron transporting materials may be used in combination with one or more other electron transporting materials or in combination with a metal such as an alkali metal or an alkaline earth metal. The ionization potential of the electron transporting layer is preferably, but not limited to, from 5.8 eV to 8.0 eV, more preferably from 6.0 eV to 7.5 eV.

Each layer of the light emitting device may be formed by any method such as resistance heating evaporation, electron beam evaporation, sputtering, molecular stacking, or coating. In view of device characteristics, resistance heating evaporation or electron beam evaporation is generally preferred.

The thickness of the organic layer may be selected from the range of 1 to 1,000 nm, while it depends on the resistance of the emissive substance and therefore cannot be limited. The thickness of each of the emissive layer, the electron transporting layer and the hole transporting layer is preferably from 1 nm to 200 nm, more preferably from 5 nm to 100 nm.

The light emitting device of the invention has the function of converting electric energy into light. Direct current is generally used as the electric energy. However, pulsed current or alternating current may also be used. The current value and the voltage value are not particularly limited. In view of the power consumption and life of the device, the current value and the voltage value should be selected so that maximum luminance can be obtained using as low energy as possible.

For example, the light emitting device of the invention is preferably used for matrix displays and/or segment displays.

In matrix displays, display pixels are arranged in a two-dimensional pattern such as a grid or mosaic pattern, and a set of pixels are used to display characters and images. The shape and size of the pixels are determined according to the intended use. For example, rectangle pixels each with a side of 300 μm or less are generally used to display characters and images on personal computers, monitors, or televisions. On the other hand, pixels each with a side of the order of millimeters may be used in large screen displays such as display panels. In a monochrome display, pixels of the same color may be arranged. In a color display, red, green and blue pixels are arranged and used for display. In this case, there are typically a delta type and a stripe type. The matrix driving method may be any of passive matrix driving and active matrix driving. The passive matrix driving structure is relatively simple. In view of operating characteristics, however, active matrix driving may be better. Therefore, they should be selectively used depending on the intended use.

In an embodiment of the invention, segment displays are displays in which a pattern is formed so that predetermined information can be displayed, and a region defined by the pattern formation is used to emit light. Examples of segment displays include time or temperature displays for digital clocks or thermometers, operation displays for audio apparatuses, electromagnetic cookers and so on, and panel displays for automobiles. The matrix display and the segment display may also be arranged in the same panel.

The light emitting device of the invention is also preferably used as a backlight for various apparatuses. The backlight is generally used for the purpose of improving the visibility of non-self-emitting displays. The backlight may be used for liquid crystal displays, clocks, audio apparatuses, motor car panels, sign boards, signs, and so on. In particular, the light emitting device of the invention is preferably used for a liquid crystal display, specifically a personal computer backlight for which a reduction in thickness has been studied, so that a backlight thinner and lighter than a conventional one can be provided.

EXAMPLES

The invention is more specifically described by the examples below, which are not intended to limit the scope of the invention. The compound number in each example corresponds to the compound number attached to each chemical formula shown above. Evaluation methods for structural analysis are described below.

$^1$H-NMR measurement was performed on a deuterated chloroform solution with Superconducting FTNMR EX-270 (manufactured by JEOL Ltd.).

HPLC purity measurement was performed on a 0.1 g/L chloroform solution with a high-performance liquid chromatographic system LC-10 (manufactured by Shimadzu Corporation). The eluent used for the separation on the column was a mixed solution of an aqueous 0.1% phosphoric acid solution and acetonitrile.

Synthesis Example 1

Synthesis of Compound [22]

A mixed solution of 45 g of 1-bromopyrene, 21.7 g of 4-methylphenylboronic acid, 34 g of tribasic potassium phosphate, 10.3 g of tetrabutylammonium bromide, 0.71 g of palladium acetate, and 1.6 l (liters) of dimethylformamide was heated and stirred at 120° C. for 5 hours under a nitrogen stream. After the mixture was cooled to room temperature, 1.6 l of water was added thereto and stirred at room temperature for 0.5 hours. The precipitated solid was separated by filtration and washed twice with 200 ml of water. The resulting solid was dissolved in 500 ml of dichloromethane. The solution was dried over magnesium sulfate and then filtered through celite. The filtrate was evaporated, and the resulting residue was washed twice with 200 ml of methanol. The precipitated solid was separated by filtration and dried under vacuum to give 40 g of 1-(4-methylphenyl)pyrene.

A mixed solution of 40 g of 1-(4-methylphenyl)pyrene, 24.4 g of N-bromosuccinimide and 1.4 l of dimethylformamide was then heated and stirred at 40° C. for 7 hours under a nitrogen stream. After the mixture was cooled to room temperature, 1 l (liter) of water was added thereto, and the mixture was extracted with 500 ml of dichloromethane. The organic layer was washed twice with 200 ml of water, dried over magnesium sulfate, and then filtered through celite. The filtrate was evaporated, and the resulting residue was washed twice with 200 ml of ethyl acetate. The precipitated solid was separated by filtration and dried under vacuum to give 11.4 g of 1-bromo-6-(4-methylphenyl)pyrene.

A mixed solution of 1.3 g of 1-bromo-6-(4-methylphenyl)pyrene, 1.55 g of 4-[4-(4,4,5,5-tetramethyl-[1,3,2]dioxaborolane-2-yl)phenyl]dibenzofuran, 1.78 g of tribasic potassium phosphate, 338 mg of tetrabutylammonium bromide, 24 mg of palladium acetate, and 35 ml of dimethylformamide was then heated and stirred at 130° C. for 5 hours under a nitrogen stream. After the mixture was cooled to room temperature, the resulting crystal was separated by filtration. The crystal was washed sequentially with 10 ml of dimethylformamide, 30 ml of water, and 30 ml of ethanol. Thereafter, 150 ml of toluene was added to the crystal, and the crystal was dissolved at 140° C. The solution was cooled to 100° C. and then filtered through celite. The filtrate was evaporated, and 50 ml of methanol was added to the residue, and filtration was performed. The product was dried under vacuum to give 1.1 g of a yellow-white crystal. The result of $^1$H-NMR analysis of the resulting powder was as shown below, and the resulting yellow-white crystal was identified as compound [22].

$^1$H-NMR (CDCl$_3$ (d=ppm)): 2.52 (s, 3H), 7.38-8.37 (m, 23H).

Compound [22] was purified by sublimation under a pressure of 1×10$^{-3}$ Pa at about 240° C. using an oil diffusion pump, before it was used as a light emitting device material. The HPLC purity (the area percentage at a measurement wavelength of 254 nm) of compound [22] was 99% and 99.9% before and after the purification by sublimation, respectively.

Synthesis Example 2

Synthesis of Compound [7]

A light yellow crystal was obtained using the process of Synthesis Example 1, except that 3-(4,4,5,5-tetramethyl-[1,3,2]dioxaborolane-2-yl)dibenzofuran was used in place of 4-[4-(4,4,5,5-tetramethyl-[1,3,2]dioxaborolane-2-yl)phenyl]dibenzofuran. The result of $^1$H-NMR analysis of the resulting powder was as shown below, and the resulting light yellow crystal was identified as compound [7].

$^1$H-NMR (CDCl$_3$ (d=ppm)): 2.52 (s, 3H), 7.38-7.66 (m, 8H), 7.86 (s, 1H), 7.98-8.26 (m, 10H).

Compound [7] was purified by sublimation under a pressure of 1×10$^{-3}$ Pa at about 230° C. using an oil diffusion pump, before it was used as a light emitting device material.

The HPLC purity (the area percentage at a measurement wavelength of 254 nm) of compound [7] was 99.2% and 99.5% before and after the purification by sublimation, respectively.

Synthesis Example 3

Synthesis of Compound [28]

A light yellow crystal was obtained using the process of Synthesis Example 1, except that 2-naphthaleneboronic acid was used in place of 4-methylphenylboronic acid. The result of $^1$H-NMR analysis of the resulting powder was as shown below, and the resulting light yellow crystal was identified as compound [28].
$^1$H-NMR (CDCl$_3$ (d=ppm)): 7.37-8.39 (m, 26H).
Compound [28] was purified by sublimation under a pressure of 1×10$^{-3}$ Pa at about 280° C. using an oil diffusion pump, before it was used as a light emitting device material. The HPLC purity (the area percentage at a measurement wavelength of 254 nm) of compound [28] was 99.1% and 99.3% before and after the purification by sublimation, respectively.

Synthesis Example 4

Synthesis of Compound [36]

A light yellow crystal was obtained using the process of Synthesis Example 1, except that 4-biphenylboronic acid was used in place of 4-methylphenylboronic acid. The result of $^1$H-NMR analysis of the resulting powder was as shown below, and the resulting light yellow crystal was identified as compound [36].
$^1$H-NMR (CDCl$_3$ (d=ppm)): 7.37-8.39 (m, 28H).
Compound [36] was purified by sublimation under a pressure of 1×10$^{-3}$ Pa at about 280° C. using an oil diffusion pump, before it was used as a light emitting device material. The HPLC purity (the area percentage at a measurement wavelength of 254 nm) of compound [36] was 99.1% and 99.3% before and after the purification by sublimation, respectively.

Synthesis Example 5

Synthesis of Compound [132]

A mixed solution of 4.1 g of pyrene, 2 g of tert-butyl chloride and 33 ml of dichloromethane was cooled to 0° C. under a nitrogen stream, and 2.7 g of aluminum chloride was added thereto. After the mixed solution was stirred at room temperature for 3 hours, 30 ml of water was added thereto, and the mixture was extracted with 30 ml of dichloromethane. The organic layer was washed twice with 20 ml of water, dried over magnesium sulfate and then evaporated. The resulting residue was purified by silica gel column chromatography and dried under vacuum to give 3 g of 2-tert-butylpyrene (65% content).
A mixed solution of 3 g of 2-tert-butylpyrene (65% content), 50 ml of dichloromethane and 15 ml of methanol was then cooled to 0° C. under a nitrogen stream, and a solution of 3.3 g of benzyltrimethylammonium tribromide in 10 ml of dichloromethane was added dropwise to the mixed solution. After the mixed solution was stirred at room temperature for 2 hours, 50 ml of water was added thereto, and the mixture was extracted with 50 ml of dichloromethane. The organic layer was washed twice with 50 ml of water, dried over magnesium sulfate, and then evaporated. Ten ml of methanol was added to the resulting solid and stirred for 10 minutes, and then the solid was separated by filtration. Thereafter, 30 ml of hexane was further added to the solid and stirred for 30 minutes, and then the solid was separated by filtration. The solid was dried under vacuum to give 2.3 g of 1-bromo-7-tert-butylpyrene.
A mixed solution of 2.3 g of 1-bromo-7-tert-butylpyrene, 1.1 g of phenylboronic acid, 3.8 g of tribasic potassium phosphate, 0.58 g of tetrabutylammonium bromide, 12 mg of palladium acetate, and 30 ml of dimethylformamide was then heated and stirred at 130° C. for 2 hours under a nitrogen stream. After the mixture was cooled to room temperature, 30 ml of water was added thereto, and the mixture was extracted with 50 ml of dichloromethane. The organic layer was washed twice with 20 ml of water, dried over magnesium sulfate, and then evaporated. The resulting residue was purified by silica gel column chromatography and dried under vacuum to give 1.5 g of 7-tert-butyl-1-phenylpyrene.
A mixed solution of 1.5 g of 7-tert-butyl-1-phenylpyrene, 25 ml of dichloromethane and 8 ml of methanol was then cooled to 0° C. under a nitrogen stream, and a solution of 1.7 g of benzyltrimethylammonium tribromide in 5 ml of dichloromethane was added dropwise to the mixed solution. After the mixed solution was stirred at room temperature for 2 hours, 20 ml of water was added thereto, and the mixture was extracted with 20 ml of dichloromethane. The organic layer was washed twice with 20 ml of water, dried over magnesium sulfate, and then evaporated. Ten ml of methanol was added to the resulting solid and allowed to stand overnight. The precipitated solid was separated by filtration and dried under vacuum to give 1.9 g of 1-bromo-7-tert-butyl-3-phenylpyrene.
A mixed solution of 696 mg of 1-bromo-7-tert-butyl-3-phenylpyrene, 815 mg of 4-[4-(4,4,5,5-tetramethyl-[1,3,2]dioxaborolane-2-yl)phenyl]dibenzofuran, 934 mg of tribasic potassium phosphate, 161 mg of tetrabutylammonium bromide, 11 mg of palladium acetate, and 17 ml of dimethylformamide was then heated and stirred at 130° C. for 5 hours under a nitrogen stream. After the mixture was cooled to room temperature, 40 ml of water was added, and filtration was performed. The product was washed with 40 ml of methanol, then purified by silica gel chromatography, and dried under vacuum to give 818 mg of a white crystal. The result of $^1$H-NMR analysis of the resulting powder was as shown below, and the resulting white crystal was identified as compound [132].
$^1$H-NMR (CDCl$_3$ (d=ppm)): 1.60 (s, 9H), 7.35-8.36 (m, 23H).
Compound [132] was purified by sublimation under a pressure of 1×10$^{-3}$ Pa at about 240° C. using an oil diffusion pump, before it was used as a light emitting device material. The HPLC purity (the area percentage at a measurement wavelength of 254 nm) of compound [132] was 99.7% and 99.8% before and after the purification by sublimation, respectively.

Synthesis Example 6

Synthesis of Compound [140]

A white crystal was obtained using the process of Synthesis Example 5, except that 2-naphthaleneboronic acid was used in place of phenylboronic acid. The result of $^1$H-NMR analysis of the resulting powder was as shown below, and the resulting white crystal was identified as compound [140].

$^1$H-NMR (CDCl$_3$ (d=ppm)): 1.61 (s, 9H), 7.24-8.38 (m, 25H).

Compound [140] was purified by sublimation under a pressure of 1×10$^{-3}$ Pa at about 270° C. using an oil diffusion pump, before it was used as a light emitting device material. The HPLC purity (the area percentage at a measurement wavelength of 254 nm) of compound [140] was 99.8% and 99.9% before and after the purification by sublimation, respectively.

Synthesis Example 7

Synthesis of Compound [124]

A white crystal was obtained using the process of Synthesis Example 5, except that 4-dibenzofuranboronic acid was used in place of phenylboronic acid and that 4-dibenzofuranboronic acid was used in place of 4-[4-(4,4,5,5-tetramethyl-[1,3,2]dioxaborolane-2-yl)phenyl]dibenzofuran. The result of $^1$H-NMR analysis of the resulting powder was as shown below, and the resulting white crystal was identified as compound [124].

$^1$H-NMR (CDCl$_3$ (d=ppm)): 1.60 (s, 9H), 7.31-7.77 (m, 10H), 7.98-8.31 (m, 11H).

Compound [124] was purified by sublimation under a pressure of 1×10$^{-3}$ Pa at about 250° C. using an oil diffusion pump, before it was used as a light emitting device material. The HPLC purity (the area percentage at a measurement wavelength of 254 nm) of compound [124] was 99.3% and 99.4% before and after the purification by sublimation, respectively.

Synthesis Example 8

Synthesis of Compound [138]

A white crystal was obtained using the process of Synthesis Example 5, except that 4-biphenylboronic acid was used in place of phenylboronic acid. The result of $^1$H-NMR analysis of the resulting powder was as shown below, and the resulting white crystal was identified as compound [138].

$^1$H-NMR (CDCl$_3$ (d=ppm)): 1.61 (s, 9H), 7.37-8.38 (m, 27H).

Compound [138] was purified by sublimation under a pressure of 1×10$^{-3}$ Pa at about 270° C. using an oil diffusion pump, before it was used as a light emitting device material. The HPLC purity (the area percentage at a measurement wavelength of 254 nm) of compound [138] was 99.7% and 99.8% before and after the purification by sublimation, respectively.

Synthesis Example 9

Synthesis of Compound [163]

A light yellow crystal was obtained using the process of Synthesis Example 1, except that 2-[4-(4,4,5,5-tetramethyl-[1,3,2]dioxaborolane-2-yl)phenyl]dibenzofuran was used in place of 4-[4-(4,4,5,5-tetramethyl-[1,3,2]dioxaborolane-2-yl)phenyl]dibenzofuran. The result of $^1$H-NMR analysis of the resulting powder was as shown below, and the resulting light yellow crystal was identified as compound [163].

$^1$H-NMR (CDCl$_3$ (d=ppm)): 2.52 (s, 3H), 7.38-8.31 (m, 23H).

Compound [163] was purified by sublimation under a pressure of 1×10$^{-3}$ Pa at about 240° C. using an oil diffusion pump, before it was used as a light emitting device material. The HPLC purity (the area percentage at a measurement wavelength of 254 nm) of compound [163] was 99.5% and 99.7% before and after the purification by sublimation, respectively.

Synthesis Example 10

Synthesis of Compound [21]

A mixed solution of 9.4 g of 1-bromopyrene, 4.5 g of phenylboronic acid, 13 g of cesium carbonate, 348 mg of (tri-tert-butylphosphine) tetrafluoroborate, 575 mg of bis(dibenzylideneacetone)palladium(0), and 33 ml of 1,4-dioxane was heated and stirred at 100° C. for 3 hours under a nitrogen stream. The solution was cooled to room temperature and then filtered through celite. The filtrate was evaporated, and the resulting concentrate was purified by silica gel column chromatography and dried under vacuum to give 7.8 g of 1-phenylpyrene.

A mixed solution of 7.8 g of 1-phenylpyrene, 5.0 g of N-bromosuccinimide and 140 ml of dimethylformamide was then heated and stirred at 50° C. for 6 hours under a nitrogen stream. After the mixture was cooled to room temperature, 30 ml of water was added thereto, and the mixture was extracted with 50 ml of toluene. The organic layer was washed twice with 20 ml of water, dried over magnesium sulfate, and then evaporated. The resulting residue was purified by silica gel column chromatography and dried under vacuum to give a mixture of 1-bromo-6-phenylpyrene and 1-bromo-8-phenylpyrene.

A mixed solution of 2.0 g of a mixture of 1-bromo-6-phenylpyrene and 1-bromo-8-phenylpyrene, 3.1 g of 4-[4-(4,4,5,5-tetramethyl-[1,3,2]dioxaborolane-2-yl)phenyl]dibenzofuran, 3.6 g of tribasic potassium phosphate, 137 mg of PdCl$_2$(dppf).CH$_2$Cl$_2$, and 56 ml of dimethylformamide was then heated and stirred at 100° C. for 4 hours under a nitrogen stream. After the mixture was cooled to room temperature, 40 ml of water was added thereto, and filtration was performed. After the product was washed with 40 ml of methanol, 100 ml of toluene was added thereto, and the product was dissolved at 140° C. The solution was cooled to 100° C. and then filtered through celite. The filtrate was evaporated, and 50 ml of methanol was added thereto, and filtration was performed.

A mixed solution of the resulting solid and 36 ml of cyclopentyl methyl ether was then heated and stirred under reflux for 30 minutes under a nitrogen stream. The solution was cooled to room temperature with stirring and then allowed to stand overnight, and the resulting precipitate was separated by filtration. A mixed solution of the precipitate and 20 ml of cyclopentyl methyl ether was heated and stirred under reflux for 1 hour under a nitrogen stream. The solution was cooled to room temperature with stirring and then further allowed to stand overnight. The resulting precipitate was separated by filtration and dried under vacuum to give 1.0 g of a light yellow crystal. The result of $^1$H-NMR analysis of the resulting powder was as shown below, and the resulting light yellow crystal was identified as compound [21].

$^1$H-NMR (CDCl$_3$ (d=ppm)): 7.38-8.38 (m, 24H).

Compound [21] was purified by sublimation under a pressure of 1×10$^{-3}$ Pa at about 260° C. using an oil diffusion pump, before it was used as a light emitting device material. The HPLC purity (the area percentage at a measurement wavelength of 254 nm) of compound [21] was 99.7% and 99.9% before and after the purification by sublimation, respectively.

Example 1

A 150 nm-thick ITO conductive film of a size of 30×13 mm was formed as an anode on a central part of a 30×40 mm glass substrate (an electron beam deposition product, 15 Ω/square, manufactured by ASAHI GLASS CO., LTD.). The anode-carrying substrate was subjected to ultrasonic cleaning with SEMICOCLEAN (registered trademark) 56 (manufactured by Furuuchi Chemical Corporation) for 15 minutes and then washed with ultrapure water. Subsequently, the substrate was subjected to ultrasonic cleaning with isopropyl alcohol for 15 minutes, then immersed in hot methanol for 15 minutes, and then dried. Immediately before the preparation of the device, the substrate was treated with UV-ozone for 1 hour. The substrate was then placed in a vacuum deposition system, and the system was evacuated until the degree of vacuum in the system reached $5\times10^{-5}$ Pa or less. First, 10 nm of copper phthalocyanine as a hole injection material and 50 nm of 4,4'-bis(N-(1-naphthyl)-N-phenylamino)biphenyl as a hole transporting material were deposited by resistance heating evaporation. Emissive materials including compound [22] as a host material and compound D-1 represented by the formula below as a dopant material were then vapor-deposited to form a 35 nm-thick layer with a dopant concentration of 5%. Compound E-1 represented by the formula below as an electron transporting material was then deposited thereon to form a 20 nm-thick layer. Lithium was vapor-deposited with a thickness of 0.5 nm on the organic layer formed as described above. Thereafter, aluminum was then vapor-deposited with a thickness of 1000 nm to form a cathode, so that a 5×5 mm square device was obtained. In this process, each film thickness was a value indicated by a quartz oscillating thickness monitor. The resulting light emitting device was driven by direct current at 10 mA/cm². As a result, highly efficient blue light emission was observed with a luminance efficiency of 6.6 μm/W. The light emitting device was continuously driven by direct current at 10 mA/cm². As a result, the luminance half-life was 6,400 hours.

[Formula 20]

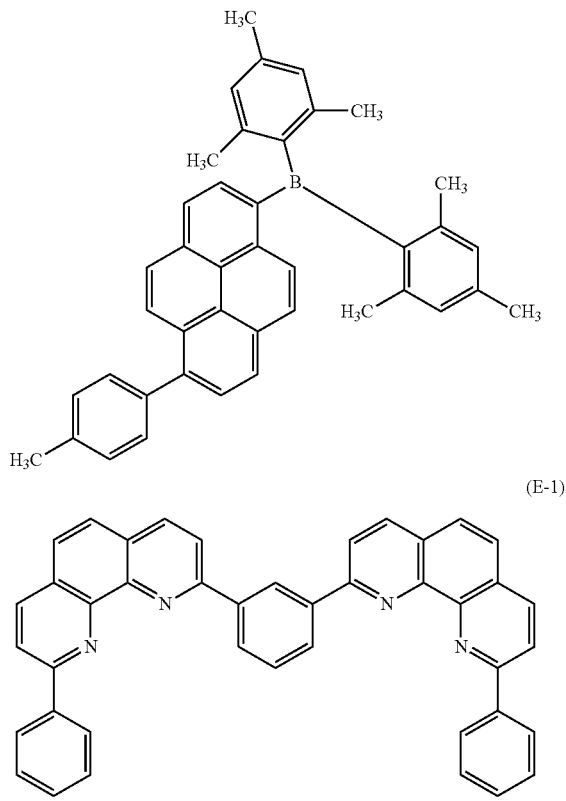

Examples 2 to 10

Light emitting devices were each prepared using the process of Example 1, except that the host materials shown in Table 1 were each used instead. The result of each example is shown in Table 1.

TABLE 1

| | Emissive Layer | | Electron Transporting Material | Color of Light Emission | Luminance Efficiency (lm/W) | Luminance half-life period (h) |
|---|---|---|---|---|---|---|
| | Host Material | Dopant Material | | | | |
| Example 1 | Compound[22] | D-1 | E-1 | Blue | 6.6 | 6400 |
| Example 2 | Compound[7] | D-1 | E-1 | Blue | 5.2 | 4500 |
| Example 3 | Compound[28] | D-1 | E-1 | Blue | 6.7 | 6300 |
| Example 4 | Compound[36] | D-1 | E-1 | Blue | 6.5 | 6000 |
| Example 5 | Compound[132] | D-1 | E-1 | Blue | 5.8 | 5500 |
| Example 6 | Compound[140] | D-1 | E-1 | Blue | 6.3 | 6000 |
| Example 7 | Compound[124] | D-1 | E-1 | Blue | 5.1 | 4000 |
| Example 8 | Compound[138] | D-1 | E-1 | Blue | 6.0 | 5500 |
| Example 9 | Compound[163] | D-1 | E-1 | Blue | 6.1 | 5800 |
| Example 10 | Compound[21] | D-1 | E-1 | Blue | 6.7 | 6600 |
| Comparative Example 1 | H-1 | D-1 | E-1 | Blue | 3.0 | 400 |
| Comparative Example 2 | H-2 | D-1 | E-1 | Blue | 3.3 | 100 |
| Comparative Example 3 | H-3 | D-1 | E-1 | Blue | 3.1 | 440 |
| Comparative Example 4 | H-4 | D-1 | E-1 | Blue | 3.8 | 800 |
| Comparative Example 5 | H-5 | D-1 | E-1 | Blue | 3.4 | 800 |
| Comparative Example 6 | H-6 | D-1 | E-1 | Blue | 3.4 | 700 |
| Comparative Example 7 | H-7 | D-1 | E-1 | Blue | 3.1 | 1200 |

Comparative Example 1

A light emitting device was prepared using the process of Example 1, except that compound H-1 represented by the formula below was used as the host material. The resulting light emitting device was driven by direct current at 10 mA/cm². As a result, blue light emission was observed with a luminance efficiency of 3.0 μm/W. The light emitting device was continuously driven by direct current at 10 mA/cm². As a result, the luminance half-life was 400 hours.

[Formula 21]

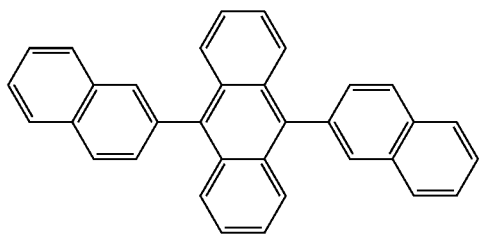
(H-1)

Comparative Examples 2 to 7

Light emitting devices were each prepared using the process of Example 1, except that the host materials shown in Table 1 were each used instead. The result of each comparative example is shown in Table 1. In Table 1, H-2, H-3, H-4, H-5, H-6, and H-7 are the compounds represented by the formulae below, respectively.

[Formula 22]

(H-2)

(H-3)

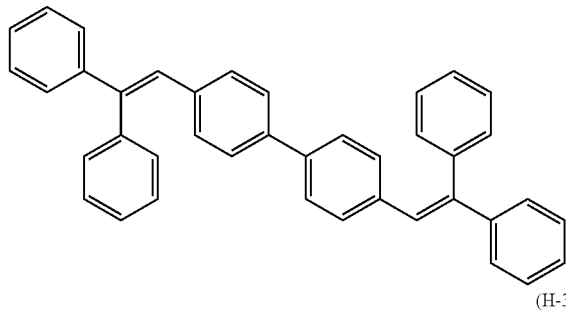

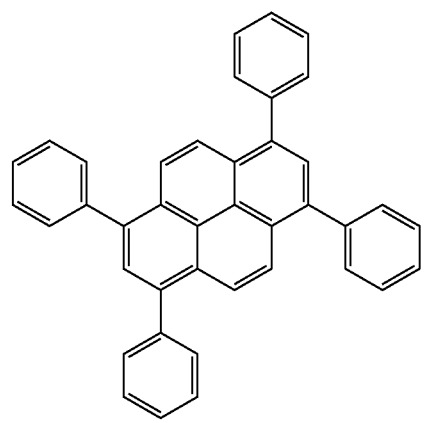

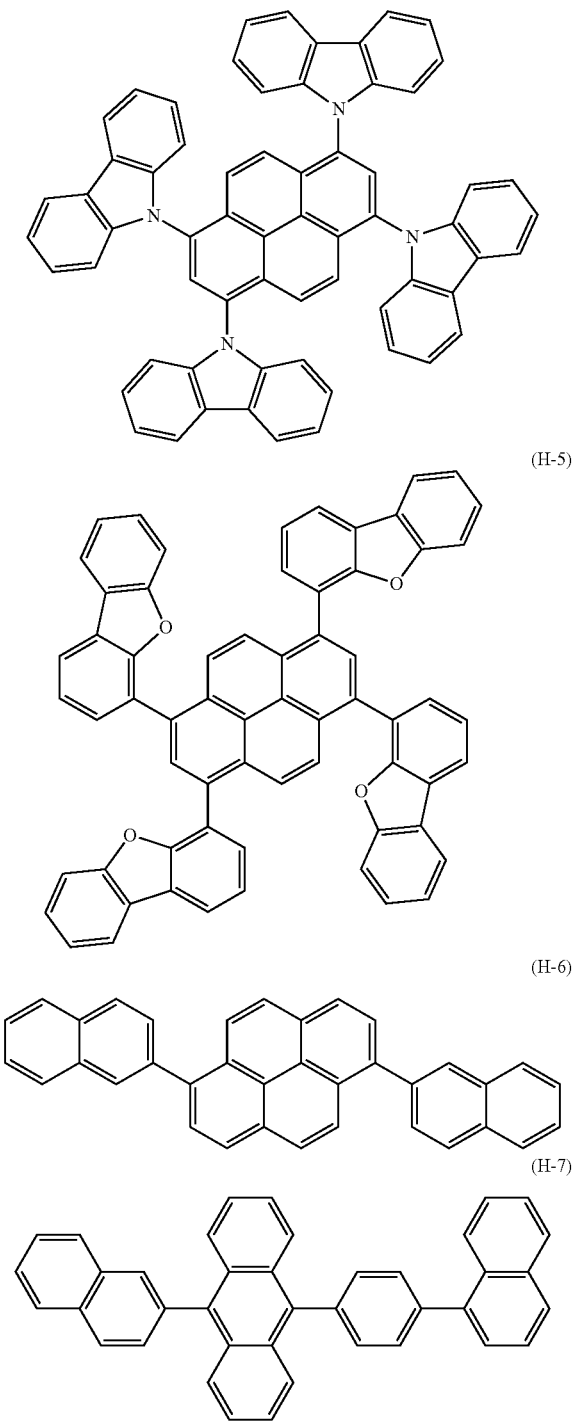

(H-4)

(H-5)

(H-6)

(H-7)

Example 11

A light emitting device was prepared using the process of Example 1, except that compound D-2 represented by the formula below was used as the dopant material so as to provide a dopant concentration of 2%. The resulting light emitting device was driven by direct current at 10 mA/cm². As a result, highly efficient blue light emission was observed with a luminance efficiency of 4.7 μm/W. The light emitting device was continuously driven by direct current at 10 mA/cm². As a result, the luminance half-life was 4,500 hours.

[Formula 23]
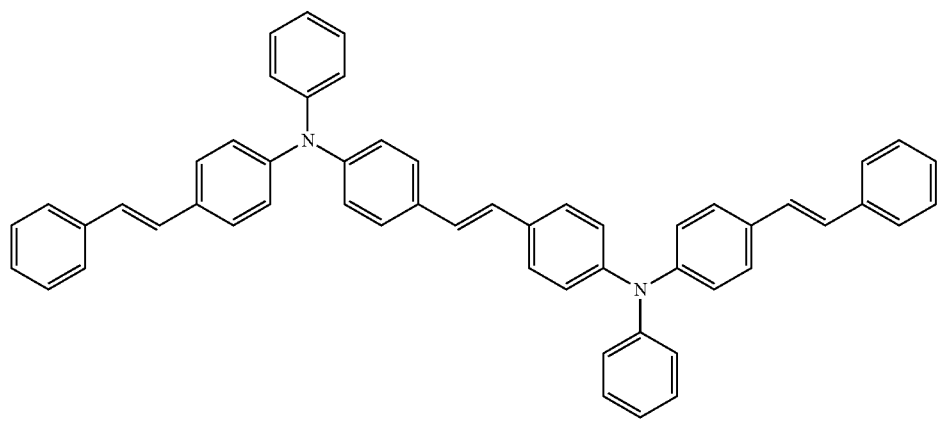
(D-2)
Examples 12 to 22
Light emitting devices were each prepared using the process of Example 1, except that the host and dopant materials shown in Table 2 were each used instead. The result of each example is shown in Table 2. In Table 2, D-3, D-4, D-5, D-6, D-7, and D-8 are the compounds represented by the formulae below, respectively.
[Formula 24]
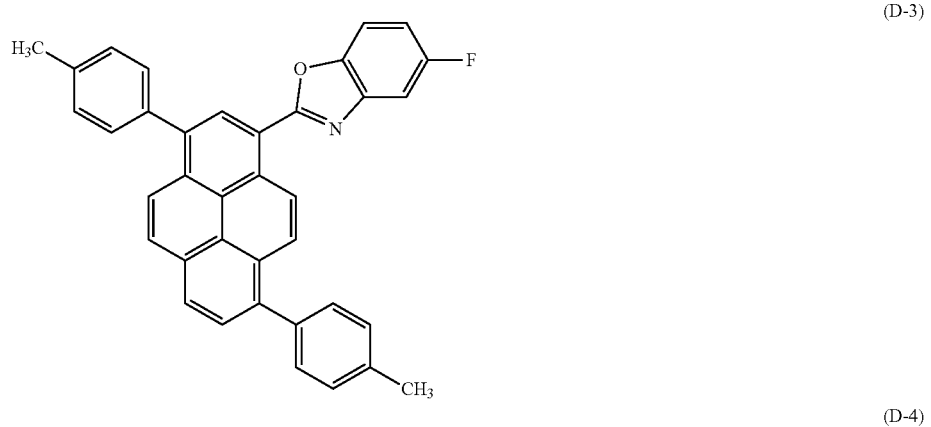
(D-3)
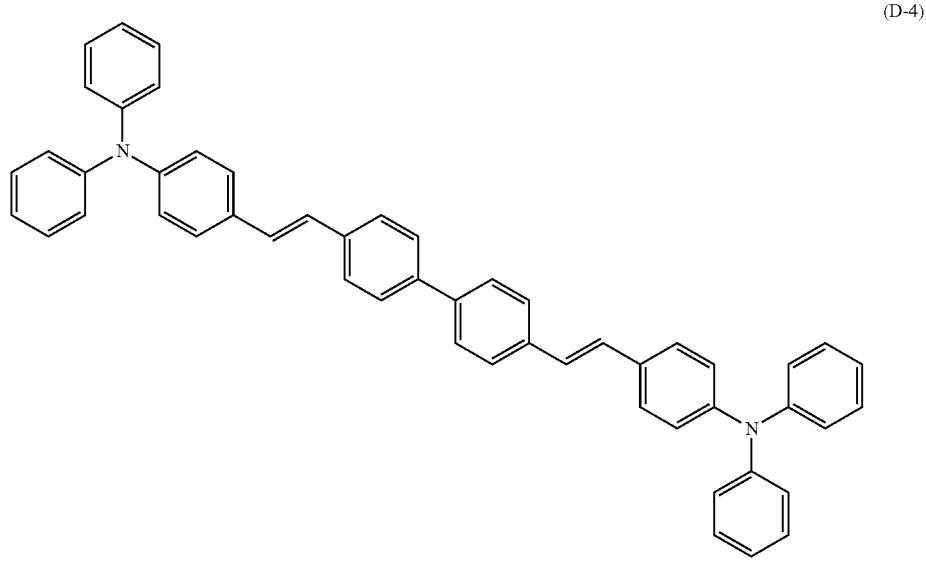
(D-4)

(D-5)
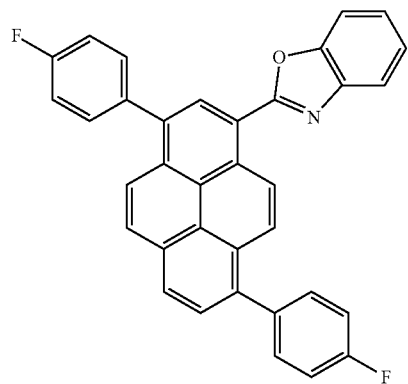
(D-6)
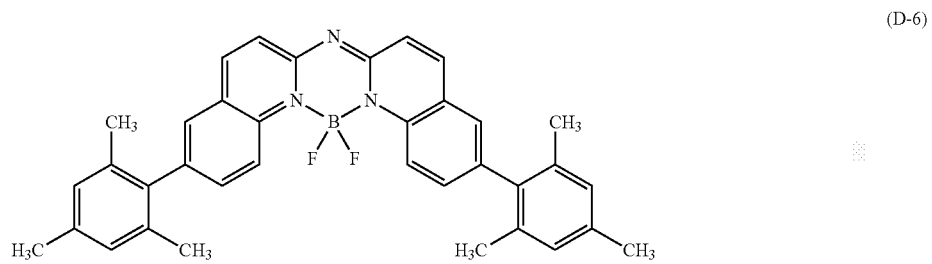
(D-7)
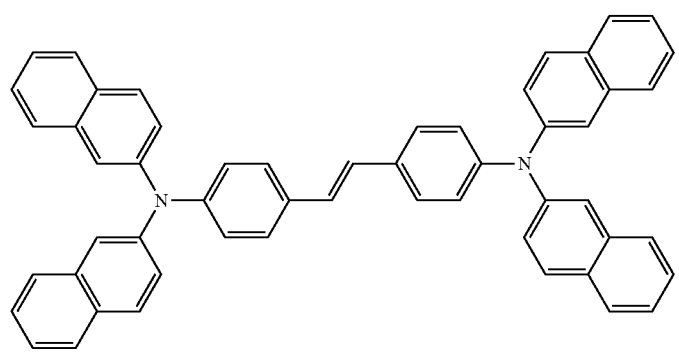
(D-8)
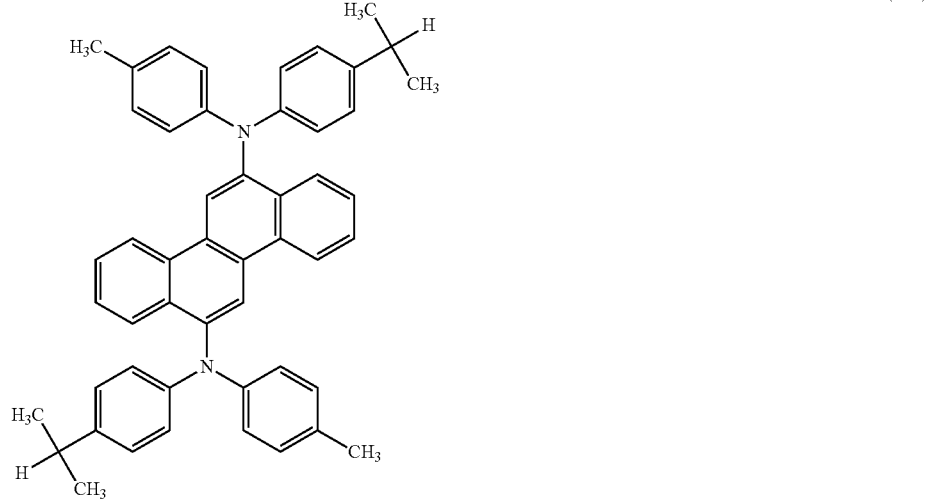

TABLE 2

|  | Emissive Layer | | Electron Transporting Material | Color of Light Emission | Luminance Efficiency (lm/W) | Luminance half-life period (h) |
| --- | --- | --- | --- | --- | --- | --- |
|  | Host Material | Dopant Material | | | | |
| Example 11 | Compound[22] | D-2 | E-1 | Blue | 4.7 | 4500 |
| Example 12 | Compound[22] | D-4 | E-1 | Blue | 4.8 | 4300 |
| Example 13 | Compound[22] | D-5 | E-1 | Blue | 4.9 | 4900 |
| Example 14 | Compound[22] | D-6 | E-1 | Blue | 5.0 | 5500 |
| Example 15 | Compound[132] | D-3 | E-1 | Blue | 5.1 | 5000 |
| Example 16 | Compound[132] | D-7 | E-1 | Blue | 4.9 | 4800 |
| Example 17 | Compound[140] | D-3 | E-1 | Blue | 5.4 | 5800 |
| Example 18 | Compound[140] | D-7 | E-1 | Blue | 5.2 | 5500 |
| Example 19 | Compound[140] | D-8 | E-1 | Blue | 5.1 | 5600 |
| Example 20 | Compound[21] | D-3 | E-1 | Blue | 5.9 | 6500 |
| Example 21 | Compound[21] | D-7 | E-1 | Blue | 5.5 | 5800 |
| Example 22 | Compound[21] | D-8 | E-1 | Blue | 5.4 | 6000 |

Example 23

A light emitting device was prepared using the process of Example 1, except that compound E-2 represented by the formula below was used as the electron transporting material. The resulting light emitting device was driven by direct current at 10 mA/cm$^2$. As a result, highly efficient blue light emission was observed with a luminance efficiency of 3.3 μm/W. The light emitting device was continuously driven by direct current at 10 mA/cm$^2$. As a result, the luminance half-life was 3,200 hours.

[Formula 25]

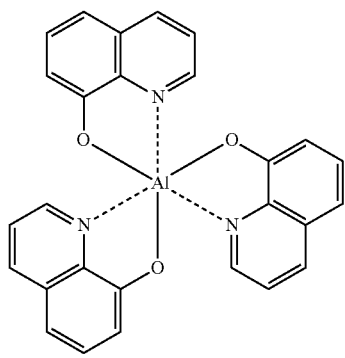

(E-2)

Examples 24 to 31

Light emitting devices were each prepared using the process of Example 1, except that the host and electron transporting materials shown in Table 3 were each used instead. The result of each example is shown in Table 3. In Table 3, E-3, E-4, E-5, E-6, and E-7 are the compounds represented by the formulae below, respectively.

[Formula 26]

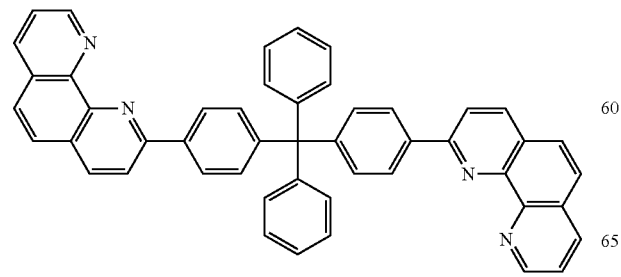

(E-3)

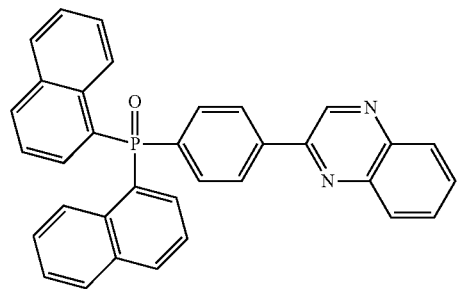

(E-4)

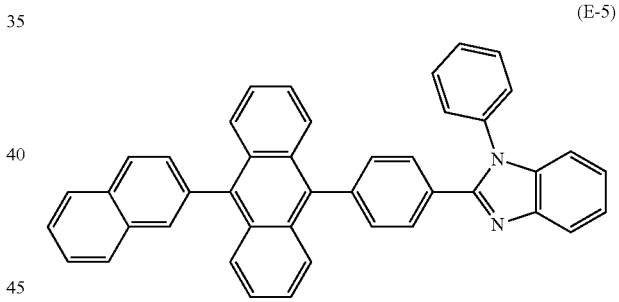

(E-5)

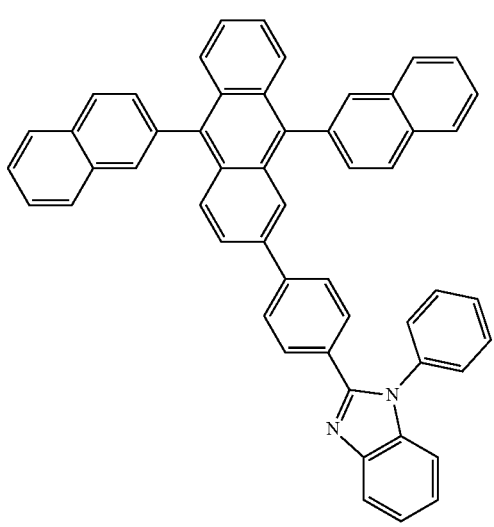

(E-6)

-continued

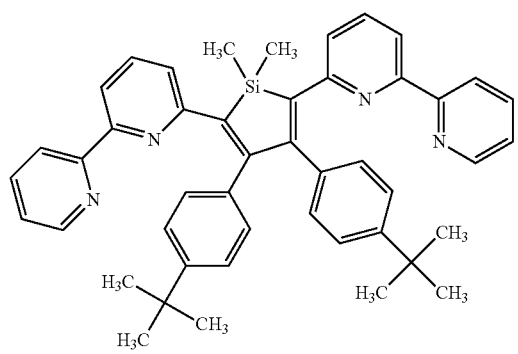

(E-7)

[Formula 27]

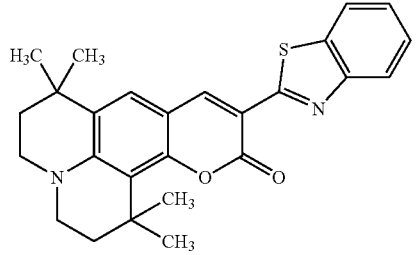

(D-9)

TABLE 3

|  | Emissive Layer | | Electron Transporting Material | Color of Light Emission | Luminance Efficiency (lm/W) | Luminance half-life period (h) |
| --- | --- | --- | --- | --- | --- | --- |
|  | Host Material | Dopant Material |  |  |  |  |
| Example 23 | Compound[22] | D-1 | E-2 | Blue | 3.3 | 3200 |
| Example 24 | Compound[22] | D-1 | E-3 | Blue | 5.2 | 5000 |
| Example 25 | Compound[22] | D-1 | E-4 | Blue | 5.8 | 5400 |
| Example 26 | Compound[140] | D-1 | E-5 | Blue | 5.5 | 5000 |
| Example 27 | Compound[140] | D-1 | E-6 | Blue | 5.0 | 5500 |
| Example 28 | Compound[140] | D-1 | E-7 | Blue | 5.9 | 5500 |
| Example 29 | Compound[21] | D-1 | E-5 | Blue | 5.7 | 6000 |
| Example 30 | Compound[21] | D-1 | E-6 | Blue | 5.3 | 5800 |
| Example 31 | Compound[21] | D-1 | E-7 | Blue | 6.1 | 5600 |

Example 32

A light emitting device was prepared using the process of Example 1, except that no dopant material was used. The resulting light emitting device was driven by direct current at 10 mA/cm$^2$. As a result, blue light emission was observed with a luminance efficiency of 1.2 μm/W. The light emitting device was continuously driven by direct current at 10 mA/cm$^2$. As a result, the luminance half-life was 3,500 hours.

Example 33

A light emitting device was prepared using the process of Example 32, except that compound [132] was used as the host material. The resulting light emitting device was driven by direct current at 10 mA/cm$^2$. As a result, blue light emission was observed with a luminance efficiency of 0.9 μm/W. The light emitting device was continuously driven by direct current at 10 mA/cm$^2$. As a result, the luminance half-life was 3,300 hours.

Example 34

A light emitting device was prepared using the process of Example 1, except that compound D-9 represented by the formula below was used as the dopant material so as to provide a dopant concentration of 5%. The resulting light emitting device was driven by direct current at 10 mA/cm$^2$. As a result, highly efficient green light emission was observed with a luminance efficiency of 6.0 μm/W. The light emitting device was continuously driven by direct current at 10 mA/cm$^2$. As a result, the luminance half-life was 5,000 hours.

Examples 35 and 36

Light emitting devices were each prepared using the process of Example 34, except that the dopant materials shown in Table 4 were each used instead. The result of each example is shown in Table 4. In the Table 4, D-10 and are the compounds represented by the formulae below, respectively.

[Formula 28]

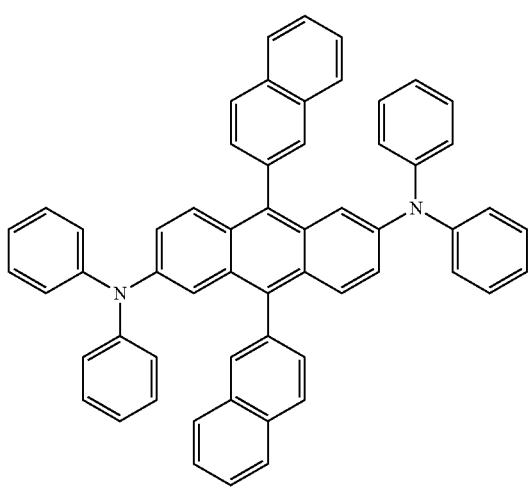

(D-10)

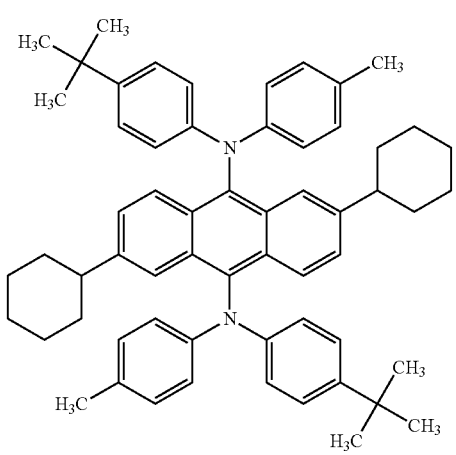

(D-11)

[Formula 29]

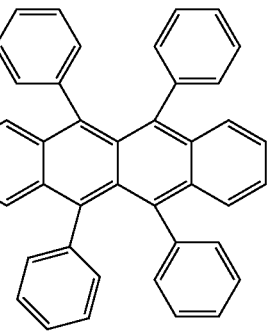

(D-12)

TABLE 4

|  | Emissive Layer | | Electron Transporting Material | Color of Light Emission | Luminance Efficiency (lm/W) | Luminance half-life period (h) |
| --- | --- | --- | --- | --- | --- | --- |
|  | Host Material | Dopant Material |  |  |  |  |
| Example 32 | Compound[22] | none | E-1 | Blue | 1.2 | 3500 |
| Example 33 | Compound[132] | none | E-1 | Blue | 0.9 | 3300 |
| Example 34 | Compound[22] | D-9 | E-1 | Green | 6.0 | 5000 |
| Example 35 | Compound[22] | D-10 | E-1 | Green | 7.0 | 6000 |
| Example 36 | Compound[22] | D-11 | E-1 | Green | 7.2 | 6500 |
| Example 37 | Compound[132] | D-9 | E-1 | Green | 5.6 | 4900 |

Example 37

A light emitting device was prepared using the process of Example 34, except that compound [132] was used as the host material. The resulting light emitting device was driven by direct current at 10 mA/cm². As a result, highly efficient green light emission was observed with a luminance efficiency of 5.6 lm/W. The light emitting device was continuously driven by direct current at 10 mA/cm². As a result, the luminance half-life was 4,900 hours.

Example 38

A light emitting device was prepared using the process of Example 1, except that emissive materials including compound [22] as a host material and compound D-1 as a dopant material were vapor-deposited to form a 5 nm-thick layer with a dopant concentration of 5%, and then emissive materials including compound [22] as a host material and compound D-12 shown below as a dopant material were deposited to form a 30 nm-thick layer with a dopant concentration of 1%. The resulting light emitting device was driven by direct current at 10 mA/cm². As a result, highly efficient white light emission was observed with a luminance efficiency of 7.0 lm/W. The light emitting device was continuously driven by direct current at 10 mA/cm². As a result, the luminance half-life was 7,100 hours.

Example 39

A light emitting device was prepared using the process of Example 38, except that compound [132] was used as the host material. The resulting light emitting device was driven by direct current at 10 mA/cm². As a result, highly efficient white light emission was observed with a luminance efficiency of 6.6 lm/W. The light emitting device was continuously driven by direct current at 10 mA/cm². As a result, the luminance half-life was 6,100 hours.

Example 40

A 150 nm-thick ITO conductive film of a size of 30×13 mm was formed as an anode on a central part of a 30×40 mm glass substrate (an electron beam deposition product, 15 Ω/square, manufactured by ASAHI GLASS CO., LTD.). The anode-carrying substrate was subjected to ultrasonic cleaning for 15 minutes with each of acetone and SEMICOCLEAN (registered trademark) 56 (manufactured by Furuuchi Chemical Corporation) and then washed with ultrapure water. Subsequently, the substrate was subjected to ultrasonic cleaning with isopropyl alcohol for 15 minutes, then immersed in hot methanol for 15 minutes, and then dried. Immediately before the preparation of the device, the substrate was treated with UV-ozone for 1 hour. The substrate was then placed in a vacuum deposition system, and the system was evacuated until the degree of vacuum in the system reached $5 \times 10^{-4}$ Pa or less. First, 150 nm of 4,4'-bis(N-(m-tolyl)-N-phenylamino) biphenyl as a hole transporting material was deposited by resistance heating evaporation. Compound [22] as a host material and compound D-1 as a dopant material were then vapor-deposited to form a 35 nm-thick layer with a dopant concentration of 5%. Compound E-1 as an electron transporting material was then deposited thereon to form a 20 nm-thick layer. In this process, each film thickness was a value indicated by a quartz oscillating thickness monitor. A 50 μm-thick kovar plate was subjected to wet etching, so that a mask having 16 apertures each 250 μm in width (50 μm in remaining part width, corresponding to 300 μm in pitch) was formed. The mask was then placed perpendicular to the ITO stripes in vacuum and fixed with a magnet placed on the back side so that the mask was attached to the ITO substrate. The organic layer was then doped with 0.5 nm of lithium, and then 200 nm of aluminum was vapor-deposited thereon so that a 32×16 dot matrix device was obtained. As a result of matrix driving of the device, characters were displayed without crosstalk.

According to one aspect of the invention, there is provided a light emitting device material that is useful for light emitting devices and so on and has high thin-film stability. According to another aspect of the invention, there is provided a light emitting device having high luminance efficiency and high durability. The light emitting device of the invention is useful in the field of display devices, flat panel displays, backlights, illuminations, interiors, signs, billboards, electro-photographic machines, optical signal generators, and so on.

What is claimed is:

1. A light emitting device material, comprising a pyrene compound represented by formula (1):

[Formula 1]

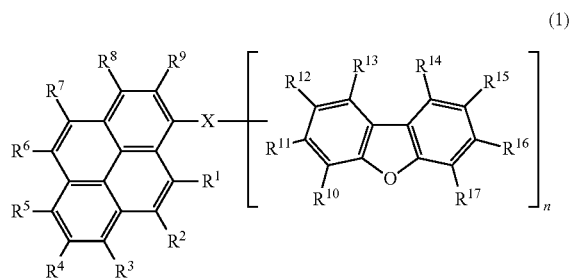

(1)

wherein
  $R^1$ to $R^{17}$ may be the same or different and are each selected from the group consisting of hydrogen, an alkyl group, a cycloalkyl group, a heterocyclic group, an alkoxy group, an alkylthio group, an aryl ether group, an aryl thioether group, an aryl group, a heteroaryl group, an amino group, a silyl group, —P(=O)$R^{18}R^{19}$, and a ring structure formed together with an adjacent substituent,
  $R^{18}$ and $R^{19}$ are each selected from an aryl group and a heteroaryl group,
  n is an integer of 1 to 2, and
  X is selected from the group consisting of a single bond, an arylene group and a heteroarylene group, provided that at least one of $R^{10}$ to $R^{17}$ is used to link to X.

2. The light emitting device material of claim 1, wherein X is an arylene group.

3. The light emitting device material of claim 1, wherein at least one of $R^3$ and $R^5$ is an aryl group or a heteroaryl group.

4. The light emitting device material of claim 1, wherein $R^3$ and $R^5$ are each hydrogen, $R^4$ is an alkyl group, and $R^8$ is an aryl group or a heteroaryl group.

5. A light emitting device, comprising an anode, a cathode and at least an emissive layer interposed between the anode and the cathode, the emissive layer emitting light by electric energy, wherein the light emitting device comprises the light emitting device material of claim 1.

6. The light emitting device of claim 5, wherein the emissive layer comprises a host material and a dopant material, and the light emitting device material represented by formula (1) is the host material.

7. The light emitting device of claim 5, further comprising at least an electron transporting layer Interposed between the emissive layer and the cathode, wherein the electron transporting layer comprises a compound having a heteroaryl ring structure comprising electron-accepting nitrogen and at least one element selected from carbon, hydrogen, nitrogen, oxygen, silicon, and phosphorus.

8. The light emitting device material of claim 2, wherein at least one of $R^3$ and $R^5$ is an aryl group or a heteroaryl group.

9. The light emitting device material of claim 2, wherein $R^3$ and $R^5$ are each hydrogen, $R^4$ is an alkyl group, and $R^8$ is an aryl group or a heteroaryl group.

* * * * *